US011576925B2

(12) United States Patent
Hui et al.

(10) Patent No.: US 11,576,925 B2
(45) Date of Patent: Feb. 14, 2023

(54) APPLICATION OF LOW-MOLECULAR-WEIGHT HYALURONIC ACID (LMW-HA) FRAGMENTS

(71) Applicant: Mizhou Hui, Shaoxing (CN)

(72) Inventors: Mizhou Hui, Shaoxing (CN); Jessica Hanitta Hui, Shaoxing (CN)

(73) Assignee: Mizhou Hui, Shaoxing (CN)

( * ) Notice: Subject to any disclaimer, the term of this patent is extended or adjusted under 35 U.S.C. 154(b) by 662 days.

(21) Appl. No.: 16/754,756

(22) PCT Filed: Apr. 25, 2017

(86) PCT No.: PCT/CN2017/081796
§ 371 (c)(1),
(2) Date: Apr. 9, 2020

(87) PCT Pub. No.: WO2017/186088
PCT Pub. Date: Nov. 2, 2017

(65) Prior Publication Data
US 2020/0254005 A1 Aug. 13, 2020

(30) Foreign Application Priority Data

Apr. 25, 2016 (CN) .......................... 201610264221.9
Apr. 24, 2017 (CN) .......................... 201710272309.X

(51) Int. Cl.
A61K 31/728 (2006.01)
A61K 47/02 (2006.01)
A61K 9/00 (2006.01)
A61K 9/08 (2006.01)

(52) U.S. Cl.
CPC ............ *A61K 31/728* (2013.01); *A61K 47/02* (2013.01); *A61K 9/0019* (2013.01); *A61K 9/08* (2013.01)

(58) Field of Classification Search
None
See application file for complete search history.

(56) References Cited

U.S. PATENT DOCUMENTS

| 9,216,164 B2* | 12/2015 | Minatelli ............... A61K 36/30 |
| 2005/0214341 A1* | 9/2005 | Brekke ............... A61L 27/3834 424/423 |
| 2006/0094643 A1* | 5/2006 | Svirkin ................ A61K 47/10 514/310 |
| 2012/0121572 A1* | 5/2012 | D'Este .................. A61P 37/06 424/94.1 |

FOREIGN PATENT DOCUMENTS

| CN | 102124019 A | 7/2011 |
| CN | 103468662 A | 12/2013 |
| CN | 104342420 A | 2/2015 |
| CN | 104546896 A | 4/2015 |
| CN | 104548106 A | 4/2015 |
| CN | 104666112 A | 6/2015 |
| CN | 104971349 A | 10/2015 |
| CN | 105018547 A | 11/2015 |
| KR | 20130143196 A | 12/2013 |
| NO | 0209728 A1 | 2/2002 |
| WO | 2014165713 A2 | 10/2014 |

OTHER PUBLICATIONS

Jaime M. Cyphert, et al., Size Matters: Molecular Weight Specificity of Hyaluronan Effects in Cell Biology, International Journal of Cell Biology, 2015, pp. 1-8, vol. 2015.
Dianhua Jiang,et al., Hyaluronan as an immune regulator in human diseases, Physiol Rev., 2011, pp. 221-264, vol. 91 No. 1.
Carlos Zgheib, et al., Targeting Inflammatory Cytokines and Extracellular Matrix Composition to Promote Wound Regeneration, Adv Wound Care (New Rochelle), 2014, pp. 344-355, vol. 3 No. 4.
Verena Voelcker, et al. Hyaluronan fragments induce cytokine and metalloprotease upregulation in human melanoma cells in part by signalling via TLR4, Experimental Dermatology,2008, pp. 100-107, vol. 17(2).
Philipp R. Esser, et al., Contact sensitizers induce skin inflammation via ROS production and hyaluronic acid degradation, PLoS One, 2012, pp. 1-16, vol. 7(7).
Katharine E Black, et al., Hyaluronan fragments induce IFNβ via a novel TLR4-TRIF-TBK1-IRF3-dependent pathway, Journal of Inflammation, 2013, pp. 2-9, vol. 10(1):23.
Maureen R. Horton, et al., Hyaluronan fragments synergize with interferon-gamma to induce the C-X-C chemokines mig and interferon-inducible protein-10 in Mouse macrophages, The Journal Of Biological Chemistry, 1998, pp. 35088-35094, vol. 273, No. 52, Issue of Dec. 25.
J Hodge-Dufour, et al., Induction of IL-12 and chemokines by hyaluronan requires adhesion-dependent priming of resident but not elicited macrophages, The Journal of Immunology, 1997, pp. 2492-2500, vol. 159(5).
Charlotte M. Mckee, et al., Hyaluronan Fragments Induce Nitric-oxide Synthase in Murine Macrophages through a Nuclear Factor kB-dependent Mechanism, The Journal Of Biological Chemistry, 1997, pp. 8013-8018, vol. 272, No. 12, Issue of Mar. 21.

(Continued)

*Primary Examiner* — Dale R Miller
(74) *Attorney, Agent, or Firm* — Bayramoglu Law Offices LLC

(57) ABSTRACT

Various pharmaceutical applications of low-molecular-weight hyaluronic acid (LMW-HA) fragments include: treating tumors, conjunctival diseases, xerophthalmia, vitreous opacity, myofascitis, arthritis, cardiovascular diseases, cerebral infaretion, dysmenorrhea, endometriosis, periodontal diseases, herpes zoster, burns, pains, pruritus, acute pancreatitis, and postoperative abdominal mucosal adhesions, helping with body recovery after chemotherapy and facial cosmesis, reducing subcutaneous fat etc. Moreover, an injection containing the LMW-HA fragments and a preparation method thereof are disclosed. The injection is injected into the subcutaneous fat layer of the abdomen for facial cosmesis and anti-aging.

2 Claims, 7 Drawing Sheets

(56) References Cited

OTHER PUBLICATIONS

Charlotte M. Mckee, et al., Hyaluronan (HA) Fragments Induce Chemokine Gene Expression in Alveolar Macrophages, The role of HA size and CD44., J. Clin. Invest. 1996, pp. 2403-2413, vol. 98, No. 10.

Sumit Ghosh, et al., Hyaluronan stimulates ex vivo B lymphocyte chemotaxis and cytokine production in a murine model of fungal allergic asthma, Immunobiology, 2015, pp. 899-909, 220(7).

Sumit Ghosh, et al., Hyaluronan deposition and co-localization with inflammatory cells and collagen in a murine model of fungal allergic asthma, Inflamm Res., 2014, pp. 475-484, 63(6).

Dragana Nikitovic, et al., Hyaluronan regulates chemical allergen-induced IL-18 production in human keratinocytes, Toxicology Letters, 2015, pp. 89-97, 232.

Christina Fieber, et al, Hyaluronan-oligosaccharide-induced transcription of metalloproteases, Journal of Cell Science, 2004, pp. 359-367, vol. 117 (2).

Giuseppe M. Campo, et al., The Inhibition of Hyaluronan Degradation Reduced Pro-Inflammatory Cytokines in Mouse Synovial Fibroblasts Subjected to Collagen-Induced Arthritis, Journal of Cellular Biochemistry, 2012, pp. 1852-1867, vol. 113(6).

G. M. Campo, et al., 4-mer hyaluronan oligosaccharides stimulate inflammation response in synovial fibroblasts in part via TAK-1 and in part via p38-MAPK, Current Medicinal Chemistry, 2013, pp. 1162-1172, vol. 20(9).

Jiurong Liang, et al. The Role of Hyaluronan and Hyaluronan Binding Proteins in Human Asthma, J Allergy Clin Immunol., 2011, pp. 403-411, vol. 128(2).

Cuixia Yang, et al., The High and Low Molecular Weight Forms of Hyaluronan Have Distinct Effects on CD44 Clustering, The Journal Of Biological Chemistry, 2012, pp. 43094-43107, vol. 287, No. 51.

Sunil R. Hingorani, et al., HALO 202: Randomized Phase II Study of PEGPH20 Plus Nab-Paclitaxel/Gemcitabine Versus Nab-Paclitaxel/Gemcitabine in Patients With Untreated, Metastatic Pancreatic Ductal Adenocarcinoma, Journal of Clinical Oncology, 2017, pp. 1-8.

Panhong Yuan, et al., Enzymatic production of specifically distributed hyaluronan oligosaccharides, Carbohydrate Polymers, 2015, pp. 194-200, vol. 129.

Edith S.A. Hofinger, et al., Recombinant human hyaluronidase Hyal-1: insect cells versus *Escherichia coli* as expression system and identification of low molecular weight inhibitors, Glycobiology, 2007, pp. 444-453, vol. 17 No. 4.

Peng Jin, et al., High-yield novel leech hyaluronidase to expedite the preparation of specific hyaluronan oligomers, Scientific Reports, 2014, pp. 1-8, vol. 4, No. 4471.

\* cited by examiner

Before Treatment   After Treatment   Before Treatment   After Treatment

After 10 Injections                After 17 Injections

Before Injection  After 6 Injections

Before Treatment  After Treatment

APPLICATION OF LOW-MOLECULAR-WEIGHT HYALURONIC ACID (LMW-HA) FRAGMENTS

CROSS REFERENCE TO THE RELATED APPLICATIONS

This application is the national phase entry of International Application No. PCT/CN2017/081796, filed on Apr. 25, 2017, which is based upon and claims priority to Chinese Patent Application No. 201610264221.9, filed on Apr. 25, 2016, and Chinese Patent Application No. 201710272309.X, filed on Apr. 24, 2017, the entire contents of which are incorporated herein by reference.

TECHNICAL FIELD

The invention relates to the application field of low-molecular-weight hyaluronic acid (LMW-HA) fragments, in particular to an application of LMW-HA fragments in preparing drugs for treating a variety of diseases and morbid conditions including solid tumors, as well as the usage in facial cosmetology and anti-aging, enhancing physical strength and energy, reducing subcutaneous fat, etc.

BACKGROUND

Hyaluronic acid (HA), also known as hyaluronan, is a long-chain polysaccharide consisted of D-glucuronic acid and N-acetylglucosamine, with the disaccharide unit up to 25 KD. Tissues such as human subcutaneous tissue, epidermis, oropharyngeal mucosa, etc. contain a large amount of high-molecular-weight hyaluronic acid (HMWV-HA). In other words, HMW-HA is the basic construction material for human skin, mucous membranes, subcutaneous tissues, etc., and it has the functions of water retention and moisturizing. The existing HA products in the market are mainly the products with HMW-HA as the main functional ingredient for facial care or facial cosmetology.

In recent years, a series of studies have suggested that LMW-HA and HMW-HA, which are distinguished by molecular weight, demonstrate functional differences in small animal experiments and cell level studies. The mainstream references have indicated that LMW-HA is a degraded byproduct of inflamed tissues and is co-located with the distribution of inflammation, and it has the function of inducing and promoting inflammatory responses. The main references include:

[1]. Jaime M. Cyphert, Carol S. Trempus, and Stavros Garantziotis, Size Matters: Molecular Weight Specificity of Hyaluronan Effects in Cell Biology (Review Article), International Journal of Cell Biology, Volume 2015 (2015), Article ID 563818.

[2]. Jiang D1, Liang J, Noble P W. Hyaluronan as an immune regulator in human diseases. Physiol Rev. 2011 January; 91(1):221-64. PMID: 21248167.

[3]. Zgheib C1, Xu J1, Liechty K Wl Targeting Inflammatory Cytokines and Extracellular Matrix Composition to Promote Wound Regeneration. Adv Wound Care (New Rochelle). 2014 Apr. 1; 3(4):344-355. PMID: 24757589.

[4]. Voelcker V1, Gebhardt C, Averbeck M, Saalbach A, Wolf V, Weih F, Sleeman J, Anderegg U, Simon J. Hyaluronan fragments induce cytokine and metalloprotease upregulation in human melanoma cells in part by signalling via TLR4. Exp Dermatol. 2008 February; 17(2): 1007. PMID: 18031543.

[5]. Esser P R1, Wlifle U, Dirr C, von Loewenich F D, Schempp C M, Freudenberg M A, Jakob T, Martin S F. Contact sensitizers induce skin inflammation via ROS production and hyaluronic acid degradation. PLoS One. 2012; 7(7):e41340. PMID: 22848468.

[6]. Black K E1, Collins S L, Hagan R S, Hamblin M J, Chan-Li Y, Hallowell R W, Powell J D, Horton M R. Hyaluronan fragments induce IFNβ via a novel TLR4-TRIF-TBK1-IRF3-dependent pathway. J Inflamm (Lond). 2013 May 30; 10(1):23. PMID: 23721397.

[7]. Horton M R1, McKee C M, Bao C, Liao F, Farber J M, Hodge-DuFour J, Pure E, Oliver B L, Wright T M, Noble P W. Hyaluronan fragments synergize with interferon-gamma to induce the C-X-C chemokines mig and interferon-inducible protein-10 in mouse macrophages. J Biol Chem. 1998 Dec. 25; 273(52):35088-94. PMID: 9857043.

[8]. Hodge-Dufour J1, Noble P W, Horton M R, Bao C, Wysoka M, Burdick M D, Strieter R M, Trinchieri G, Pure E. Induction of IL-12 and chemokines by hyaluronan requires adhesion-dependent priming of resident but not elicited macrophages. J Immunol. 1997 Sep. 1; 159(5): 2492-500. PMID: 9278343.

[9]. McKee C M1, Lowenstein C J, Horton M R, Wu J, Bao C, Chin B Y, Choi A M, Noble P W. Hyaluronan fragments induce nitric-oxide synthase in murine macrophages through a nuclear factor kappaB-dependent mechanism. J Biol Chem. 1997 Mar. 21; 272(12):8013-8. PMID: 9065473.

[10]. McKee C M1, Penno M B, Cowman M, Burdick M D, Strieter R M, Bao C, Noble P W. Hyaluronan (HA) fragments induce chemokine gene expression in alveolar macrophages. The role of HA size and CD44. J Clin Invest. 1996 Nov. 15; 98(10):2403-13. PMID: 8941660.

[11]. Ghosh S1, Hoselton S A2, Wanjara S B2, Carlson J3, McCarthy J B4, Dorsam G P2, Schuh J M2. Hyaluronan stimulates ex vivo B lymphocyte chemotaxis and cytokine production in a murine model of fungal allergic asthma. Immunobiology. 2015 Feb. 7. PMID: 25698348.

[12]. Ghosh S1, Samarasinghe A E, Hoselton S A, Dorsam G P, Schuh J M. Hyaluronan deposition and co-localization with inflammatory cells and collagen in a murine model of fungal allergic asthma. Inflamm Res. 2014 June; 63(6):475-84. PMID: 24519432.

[13]. Nikitovic D1, Berdiaki A2, Galbiati V3, Kavasi R M2, Papale A3, Tsatsakis A4, Tzanakakis G N2, Corsini E3. Hyaluronan regulates chemical allergen-induced IL-18 production in human keratinocytes. Toxicol Lett. 2014 Oct. 1; 232(1):89-97. PMID: 25280773.

[14]. Fieber C1, Baumann P. Vallon R, Termeer C, Simon J C, Hofmann M, Angel P, Herrlich P, Sleeman J P. Hyaluronan-oligosaccharide-induced transcription of metalloproteases. J Cell Sci. 2004 Jan. 15; 117(Pt 2):359-67. PMLD: 14657275.

[15]. Campo G M1, Avenoso A, D'Ascola A, Scuruchi M, Prestipino V, Nastasi G, Calatroni A, Campo S. The inhibition of hyaluronan degradation reduced pro-inflammatory cytokines in mouse synovial fibroblasts subjected to collagen-induced arthritis. J Cell Biochem. 2012 June; 113(6):1852-67. PMID: 22234777.

[16]. Campo G M1, Avenoso A, D'Ascola A, Prestipino V, Scuruchi M, Nastasi G, Calatroni A, Campo S. 4-mer hyaluronan oligosaccharides stimulate inflammation response in synovial fibroblasts in part via TAK-1 and in part via p38-MAPK. Curr Med Chem. 2013; 20(9):1162-72. PMID: 23298137.

[17]. Liang J1, Jiang D, Jung Y, Xie T, Ingram J, Church T, Degan S, Leonard M, Kraft M, Noble P W. Role of hyaluronan and hyaluronan-binding proteins in human asthma. J Allergy Clin Immunol. 2011 August; 128(2): 403-411. PMID: 21570715.

However, the applicant's research achievements in recent years (patent application No. 200780052196.7, 201310325056.X, 201310454955.X, 201410153593.5, 201510065499.9, 201510065498.4, 201510067326.0 and 201510333526.6) suggest another possibility that LMW-HA fragments in-vitro preparation have the function of inhibiting inflammation of skin and mucous membranes. According to these references, the role of the LMW-HA fragments in inhibiting inflammation may be related either to the extent of molecular size or to its manufacture method. Moreover, the comparative results of experiments on small animals, large animals and human also show that the function of the LMW-HA fragments may be completely different in small animals, large animals and human. For example, the above patent references indicated that the LMW-HA fragments with a molecular weight distribution of 10~60 KD could be prepared into in vitro preparations for topical use (such as daily necessities, hygiene products, cosmetics, skin care products, disinfecting products, etc.) to help alleviate or treat inflammation of skin and mucous membranes; whereas other's LMW-HA less than 10 KD substantially did not have such effect. However, according to the recent patent WO/2014/165713 of CEDARS-SINAI MEDICAL CENTER, LMW-HA less than 10 KD produced by use of streptococci hyaluronidase digesting HA did not induce an inflammatory reaction, but LMW-HA greater than 10 KD produced by *Streptomyces* hyaluronidase induced an inflammatory reaction, suggesting that the function of LMW-HA may also be related to the type of enzyme for digestion, namely, manufacture methods which lead to differences in the three-dimensional structure or molecular arrangement of HA fragments.

These contradictory research results suggest that it is difficult to determine the exact function of LMW-HA fragments at present. Perhaps the production mode, molecular weight, type of enzyme for digestion, the mode of use, etc. of LMW-HA fragments may affect their functional performance, but in addition to these known possible factors, there are many other unknown factors for the researchers currently, for example, reliable experimental results of large animals are not available. Therefore, although the insiders pin their hope on the medical value of LMW-HA, it is difficult to predict the clinical research and success of LMW-HA, and it is quite difficult to determine the clinical indications. A feasible and effective LMW-HA in vitro preparation has been obtained in previous researches, but due to the complex internal environment of human, the LMW-HA in vivo injection may be completely different from the in vitro preparation, whereas the role may not be the same in human, large animals and small animals. Therefore, it requires for further verification by clinical studies. In addition, LMW-HA used for in vivo injection will have higher requirements on more aspects, for example, it shall meet the requirements of high purity, no severe pain when injection or after injection and no allergic reaction, and the indications and side effects, as well as the dose of each injection, the way of injection, etc. shall be specified. It will have great scientific significance and application value in solving the above unpredictable problems.

SUMMARY

The invention aims to provide the application of LMW-HA fragments in the following aspects, including:

The application of the LMW-HA fragments in preparing drugs for treating solid tumors.

Specifically, the solid tumors include, but are not limited to, lung cancer, pancreatic cancer, oral cancer, meningioma, gastric cancer and ovarian cancer.

The application of the LMW-HA fragments in preparing drugs for treating xerophthalmia, muscae volitantes, conjunctival diseases, vitreous opacity, and vitreous detachment or impaired vision caused by vitreous opacity.

The application of the LMW-HA fragments in preparing drugs for treating myofascitis, muscle and tendon injury, hyperosteogeny, bone spur, protrusion of intervertebral disc and diseases of lumbar spinal diseases and cervical vertebra.

The application of the LMW-HA fragments in preparing drugs for treating gout, arthritis and ankylosing spondylitis.

The application of the LMW-HA fragments in preparing drugs for treating cardiovascular diseases.

The application of the LMW-HA fragments in preparing drugs for promoting the functional rehabilitation after cerebral infarction or cerebral hemorrhage.

The application of the LMW-HA fragments in preparing drugs for treating dysmenorrheal, endometriosis and adenomyosis.

The application of the LMW-HA fragments in preparing drugs for treating periodontal diseases, dental ulcer and guttural diseases.

The application of the LMW-HA fragments in preparing drugs for treating herpes zoster, neurodermatitis, psoriasis, eczema, eczema herpeticum and pompholyx.

The application of the LMW-HA fragments in preparing drugs for treating burn, trauma and surgical wound.

The application of the LMW-HA fragments in preparing drugs for treating pain or pruritus.

The application of the LMW-HA fragments in preparing drugs for treating acute pancreatitis.

The application of the LMW-HA fragments in preparing drugs for treating abdominal mucous membrane adhesion and pelvic mucous membrane adhesion after operation or peritoneal dialysis.

The application of the LMW-HA fragments in enhancing or restoring physical strength and energy after chemotherapy or in preparing drugs for treating side effects after chemotherapy.

The application of the LMW-HA fragments in facial cosmetology or in preparing drugs for treating facial aging.

The application of the LMW-HA fragments in preparing drugs for reducing subcutaneous fat tissue.

The above LMW-HA fragments are HA fragments with a molecular weight distribution of 10~60 KD, and the HA fragments are obtained from HMW-HA as raw material through recombinant human hyaluronidase PH20 after digestion.

Further, the recombinant human hyaluronidase PH20 is the recombinant human hyaluronidase produced by zooblasts or yeast or plant expression, with the purity higher than 98.5%.

Further, the LMW-HA fragments are prepared into an injection for application, and the injection contains an effective dose of HA fragments with a molecular weight distribution of 10~60 KD.

Further, the injection is injected via abdominal subcutaneous fat layer or at painful/itchy points or diseased sites.

Further, the injection is administrated 1~2 times per day, and the effective dose of HA fragments is 100~200 mg per injection.

Further, the injection is a liquid preparation, which is prepared by the following steps: A. Prepare HMW-HA raw material into solution, introduce sodium chloride and magnesium ions, and add recombinant human hyaluronidase PH-20 for digestion to obtain the injection containing HA fragments with a molecular weight distribution of 10~60 KD; B. Inactivate the residual recombinant human hyaluronidase PH20 in the obtained injection; C. Inactivate viruses and remove bacteria through 0.22 μm filtration or inactivate bacteria.

Further, the HMW-HA raw material in Step A is baked at 105° C. for 5~6 h and 120° C. for 1~2 h respectively in advance, and they are then prepared into solution.

Further, the HMW-HA raw material in Step A has a molecular weight distribution of 800~1,200 KD. 4,000~5,000 units of the recombinant human hyaluronidase PH20 are added to each 1 g of the HMW-HA raw material correspondingly for digestion, and the enzyme digestion reaction is kept for 5~6 h.

Further, the HMW-A raw material in Step A is directly prepared into solution, the HMW-HA raw material has a molecular weight distribution of 800~1,200 KD. 15,000~20,000 units of the recombinant human hyaluronidase PH20 are added to each 1 g of the HMW-HA raw material correspondingly for digestion, and the enzyme digestion reaction is kept for 5~6 h.

Further, the concentrations of sodium chloride and magnesium ions introduced in Step A in the prepared solution are 80~90 mM and 1 mM, respectively.

Further, the inactivated recombinant human hyaluronidase is also removed after Step B.

Further, each 2~4 ml of the injection contains 100 mg of HA fragments, and the residual recombinant human hyaluronidase shall not exceed 20 ug.

Further, the final concentration of magnesium ions in the injection is 1 mM, and the final concentration of sodium chloride in the injection is 115~125 mM.

Owing to the above technical schemes, the invention at least has the following advantages:

(1) Based on the experimental studies on the LMW-HA fragments for small animals, large animals and human, the invention finds that such HA fragments have a series of new applications in injection use. The experimental results show that the LMW-HA fragments have unexpected therapeutic effects on multiple diseases, as well as the efficacies of relieving pain and itching rapidly and enhancing physical strength and energy. Thus the LMW-HA fragments have great application values in preparing drugs or adjuvant drugs for treating relevant diseases. Besides, according to the experimental results, it can reduce subcutaneous fat, especially that of human head, face and neck; at the same time, it also has the efficacies on facial cosmetology and anti-aging, it can be injected via abdominal subcutaneous fat layer instead of facial injection, which will not result in pain and facial inflammations. Therefore, the LMW-HA fragments also have outstanding application potential in the fields of body care, anti-aging and cosmetology.

(2) The LMW-HA fragments for injection use can be prepared into a form of liquid preparation. Due to the convenient production and stable preparation, it is applicable for batch production, and no allergic reaction and side effect have occurred for human injection while in use.

BRIEF DESCRIPTION OF THE DRAWINGS

The above are only the summarization on the technical schemes of the invention. In order to get clearer understanding about the technical means, the invention will be further explained in details by combining with drawings and embodiments.

DETAILED DESCRIPTION OF THE EMBODIMENTS

Figure 1:
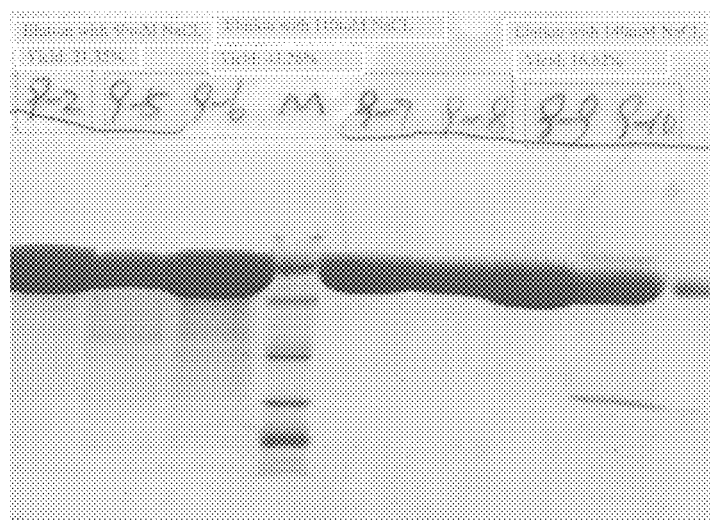
FIG. 1 is an electropherogram of high-purity glycosylated recombinant human hyaluronidase derived from CHO cells of the shaking culture bioreactor.

As mentioned above, based on the current industrial research achievements, it is difficult to determine the exact functions of LMW-HA. And there are even contradictive functional phenomena according to the results of current scientific experiments, whereas the mechanism of action for such phenomena is still completely unclear. On the basis of previous researches (patent application No. 200780052196.7, 201310325056.X, 201310454955.X, 201410153593.5, 201510065499.9, 201510065498.4, 201510067326.0 and 201510333526.6), the invention hopes to further explore the unknown functions of LMW-IH-A fragments by designing studies on small animals, large animals and human. According to the experimental studies on small animals and large animals, the inventor finds that the LMW-HA fragments in injection use have unclear therapeutic effect on species of small animals but it has a clear anti-inflammatory effect on large animals. At the same time, the results of clinical studies on human also unexpectively suggest that the LMW-HA fragments have a series of new applications in injection use, and such applications can be reflected by more convenient ways of injection (such as injection via abdominal subcutaneous fat layer or at painful/itching point or diseased sites).

The experimental results of clinical studies show that the LMW-HA fragments have an unexpected effect of treating multiple diseases or alleviating symptoms in injection use. Specifically, the multiple diseases include, but are not limited to, solid tumors (such as lung cancer, pancreatic cancer, oral cancer, meningioma, gastric cancer, ovarian cancer, etc.), xerophthalmia, muscae volitantes, conjunctival diseases, vitreous opacity, vitreous detachment or impaired vision induced by vitreous opacity, myofascitis, muscle and tendon injury, hyperosteogeny, bone spur, protrusion of intervertebral disc, diseases of lumbar spinal diseases and cervical vertebra, gout, arthritis, ankylosing spondylitis, cardiovascular diseases (including but not limited to coronary heart disease and the complications after intravascular stent), dysmenorrhea, endometriosis, adenomyosis, periodontal disease, dental ulcer and guttural diseases, herpes zoster, neurodermatitis, psoriasis, eczema, eczema herpeticum pompholyx, burn, trauma, surgical wound, etc., as well as abdominal mucous membrane adhesion, pelvic mucous membrane adhesion, etc. induced after operation or peritoneal dialysis; besides, it can prevent the transfer of solid tumors, accelerate the functional rehabilitation after cerebral infarction or cerebral hemorrhage, enhance or recover physical strength and energy after chemotherapy or treat the side effects after chemotherapy, and it can also quickly alleviate pain or pruritus; according to these results, LMW-HA fragments have a great application value in preparing drugs or adjuvant drugs for treating relevant diseases.

Besides, the experimental results also suggest that LMW-HA fragments reduce subcutaneous fat, especially that of human head, face and neck. At the same time, they also have the efficacies on facial cosmetology and anti-aging. The existing LMW-HA in the market is used by facial injection, and it is injected into dermal wrinkles and concaves or the site to be smoothed in the form of filler to realize the application for facial cosmetology, such as filling concaves, removing wrinkles, moulding, etc.; the LMW-HA fragments in the invention differ in that they can be injected via abdominal subcutaneous fat layer while in use instead of facial injection, which will not result in pain and facial inflammation. Therefore, the LMW-HA fragments also have an outstanding application potential in the fields of body care, anti-aging and cosmetology.

The LMW-HA fragments of the invention in the above experiments are obtained by the following specific manufacture method: the LMW-HA fragments are HA fragments with a molecular weight distribution of 10~60 KD obtained from LMW-HA digested directly by recombinant human hyaluronidase PH20. In the process of production, recombinant human hyaluronidase PH20 can be produced by Chinese hamster ovary (CHO) cells or yeast or plant expression, for example, it has been recorded in the previous patent application documents (publication No.: CN104342420A, CN103468662A and CN105018547A) that glycosylated recombinant human hyaluronidase PH20 is produced by using the Chinese hamster ovary (CHO) cells.

In order to ensure the safety in injection use, high purity is preferred for recombinant human hyaluronidase PH20 (preferred with a purity >98.5%), and a medical purity >98.5% is preferred for HMW-HA raw material. In practical production, raw material of high purity can be used directly, or recombinant human hyaluronidase PH20 and HI MW-HA raw material of low purity can also be used for the subsequent steps after purification. Besides, on completion of the enzyme digestion reaction, recombinant human hyaluronidase shall also be inactivated, following by inactivating viruses and filtering or inactivating bacteria. By combining with the results of clinical studies, it has been found that HA fragments containing protein residue of recombinant human hyaluronidase have no allergic reaction and side effect in injection use, but it is suggested to separate and remove the protein residue of recombinant human hyaluronidase PH20 after inactivation.

For convenience of injection use, LMW-HA fragments are prepared into a liquid injection for use during the experiments, and the injection contains an effective dose of HA fragments with a molecular weight distribution of 10~60 KD. In practical application, the LMW-HA fragments for injection use can be prepared into other forms of injection, for example, they can also be prepared into sterile powder or concentrated solution which will be mixed into solution before use.

The invention will be explained through the specific embodiments below. It shall be understood that the embodiments described here are only for describing and explaining the invention but not for limiting the invention. Besides, unless otherwise specified, the drugs or reagents involved in the following embodiments can all be purchased from normal business channel. Unless otherwise specified, the experimental techniques or operating methods involved in the following embodiments all refer to the known conventional experimental techniques or operating methods in this field.

Embodiment 1

Objective: To produce recombinant human hyaluronidase PH20 and prepare LMW-HA fragments injection Methods: Based on the methods recorded in the patent documents No. CN104342420A, CN103468662A and CN105018547A, glycosylated recombinant human hyaluronidase PH20 was produced using Chinese hamster ovary (CHO cells), including: Artificially synthesize the gene cDNA of glycosylated recombinant human hyaluronidase PH20, insert it into the empty GC-rich expression vectors of pMH3, pMH4 and pMH5 to construct the expression vectors of pMH3-PH20, pMH4-PH20 and pMH5-PH20 (the expression vectors were constructed using the methods recorded in the patent document No. CN102124019A so as to extremely highly express recombinant protein); then transfer the cDNA expression vectors of pMH3-PH20, pMH4-PH20 and pMH5~PH20 into the CHO-S cell line, and screen the CHO-S cell clones for cell lines that express the highest level of human hyaluronidase PH20. Then, the cell lines that express the highest level of human hyaluronidase PH20 was scaled up for large-scale culture in the shaking cell culture bioreactor; filter the harvested condition medium containing PH20 through 0.22 μm filtration membrane, then separate by 2~3 steps using ion column, hydrophobic column and hydroxyapatite column etc., then perform the steps of bacterial filtration, virus filtration and inactivation, ultrafiltration for preparation of concentrated purified bulk of sterile and virus-free glycosylated recombinant human hyaluronidase PH20 with a purity >99.0%.

Use an enzyme digestion and blending bioreactor with a working volume of 25 L featured with cleaning and sterilization in-place, and prepare injection-grade HA raw material with a molecular weight distribution of 800~1,200 KD; add and blend the injection-grade I-HA raw material with a molecular weight distribution of 800~1,200 KD into injection-grade pure water for intensive dissolution one time or several times; then add sodium chloride, magnesium ions and recombinant human hyaluronidase until reaching their final concentration of 80~90 mM, 1 mM and 15,000~20,000 units (about 15~20 μg) per 1 g of HMW-HA respectively in order, mix them completely, and react at 37° C. for 5~6 h until that the molecular weight of HA fragments reaches 10 KD~60 KD. Add sodium chloride at a final concentration of 35~45 mM to regulate the osmotic pressure to 280~300 mOsm/L, then heat it at 84~95° C. for 30~60 min (thermal inactivation of recombinant human hyaluronidase, partial bacterial inactivation and virus inactivation (by simultaneously reducing the pH level), and then remove bacteria by 0.22 μm filtration. Solution 1 was obtained after the filtration, and it contained the residue of inactivated recombinant human hyaluronidase. Further, remove the protein residue of inactivated recombinant human hyaluronidase PH20 in Solution 1 by using affinity column chromatography, precipitation, ultrafiltration and dialysis in order or respectively to obtain Solution 2 containing 10 KD-60 KD HA fragments, sodium chloride and magnesium ions only.

In order to research the production method of injection preparation and clearly know the effect of recombinant human hyaluronidase after inactivation, two injections containing HA fragments were obtained according to the above production method in the embodiment: one based on Solution 1 contains the protein residue of inactivated recombinant human hyaluronidase PH20 without enzyme activity (the amount of the protein residue shall be controlled in production practice for safety and reliability in use). The other one based on Solution 2 does not contain the protein residue of inactivated recombinant human hyaluronidase PH20.

Figure 2:
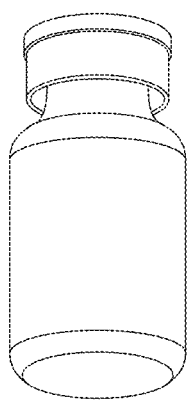
FIG. 2 is a bottled injection of HA fragments.

Results:

The glycosylated recombinant human hyaluronidase with a purity >99% and produced from CHO cells was obtained (FIG. 1);

The following two injections containing LMW-HA fragments were prepared, and the injections were filled in small bottles and prepared into HA fragments with an effective dose of 100 mg per bottle (FIG. 2). After final filling and packaging, the injections can be stably stored at 4~12° C. or −8~70° C. or room temperature for 2 years.

Injection 1: Each 2~4 ml contained 100 mg of HA fragments with a molecular weight distribution of 10 KD~60 KD and <20 μg of protein residue of inactivated recombinant human hyaluronidase PH20 without enzyme activity (endotoxin <0.5 IU/ml, sterile, virus-free), the final concentration of sodium chloride was 115~125 mM, and the final concentration of magnesium ions was 1 mM.

Injection 2: Each 2~4 ml contained 100 mg of HA fragments with a molecular weight distribution of 10 KD-60 KD but did not contain protein residue of inactivated recombinant human hyaluronidase PH20 (endotoxin <0.5 IU/ml, sterile, virus-free), the final concentration of sodium chloride was 115~125 mM, and the final concentration of magnesium ions was 1 mM.

Conclusion: The results suggest that HA fragment Injection 1 containing protein residue of recombinant human hyaluronidase and Injection 2 not containing protein residue of recombinant human hyaluronidase are successfully prepared, and the production technology for the injection of HA fragments is established.

Besides, it has been found in the following experiments that the two forms of injections have basically the same therapeutic effect, and have no allergic reaction and other side effects (which meets the FDA standards for biological medicine and Type III medical devices), suggesting that inactivated recombinant human hyaluronidase PH20 has no influence on the effect and safety of injection of HA fragments. HA fragments with a molecular weight distribution of 10 KD-60 KD is the main active ingredient in the injections, and such bioactive HA fragments (the LMW-HA fragments) are called as B-HA for short.

Embodiment 2

Objective: To study bacterial inhibition activity, in-vitro cellular activity, and activity in small animals for the above HA fragment injections (Injection 1 and Injection 2).

Methods: Dilute Injection 1 and Injection 2 with normal saline to double volume for study bacterial inhibition activity, in-vitro cellular activity, and activity in small animals of the above HA fragment injections (Injection 1 and Injection 2).

Figure 3:
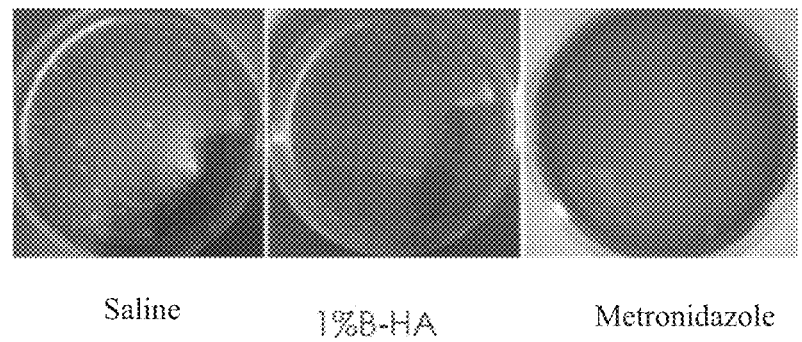
FIG. 3 shows the antibacterial effect of HA fragments with a molecular weight distribution of 10 KD-60 KD (1% B-HA in the figure means the injection treatment group treated by the injection containing 1% HA fragments with a molecular weight distribution of 10 KD-60 KD).
Figure 4:
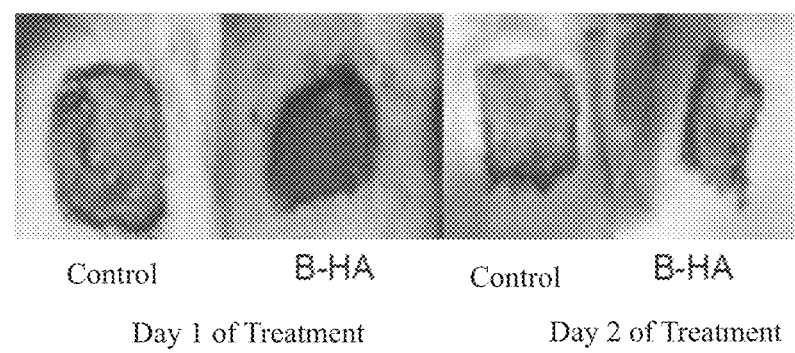
FIG. 4 shows the anti-inflammatory and antibacterial effects of the injection of the invention on the skin wound of small animal (B-HA in the figure means the injection treatment group treated by HA fragments with a molecular weight distribution of 10 KD-60 KD).
Figure 5A:
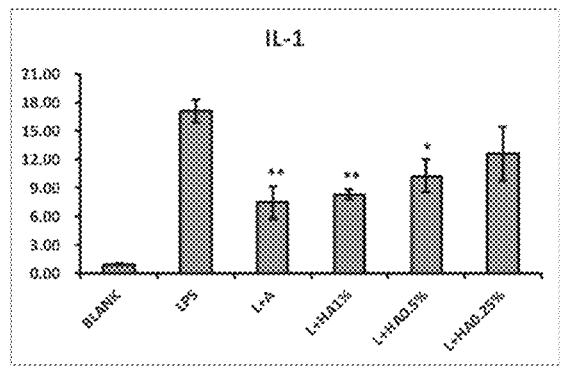
In FIG. 5A-FIG. 5E show the effects of LMW-HA fragments injection on IL-1, IL-6, IFN-β, IFN-α and IL-10, respectively (in the figure: LPS=endotoxin; L+A=LPS lipopolysaccharide+anti-human TLR4 single chain antibody; L+HA=LPS lipopolysaccharide+HA fragments with a molecular weight distribution of 10 KD-60 KD).
Figure 5B:
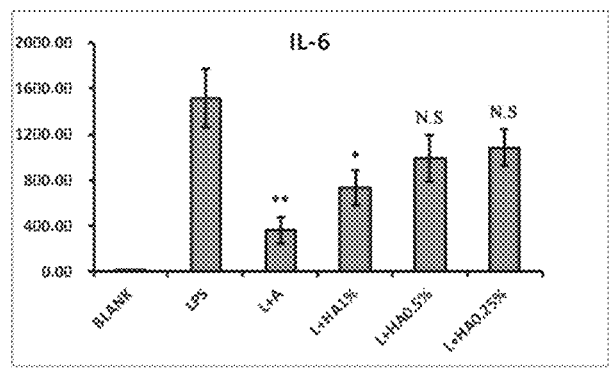
Figure 5C:
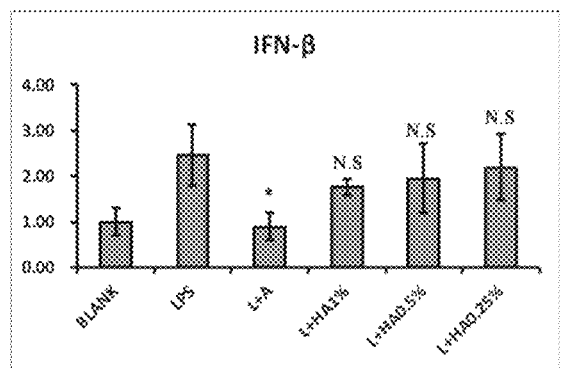
Figure 5D:
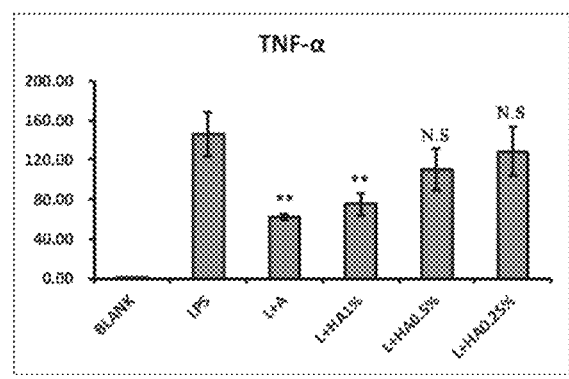
Figure 5E:
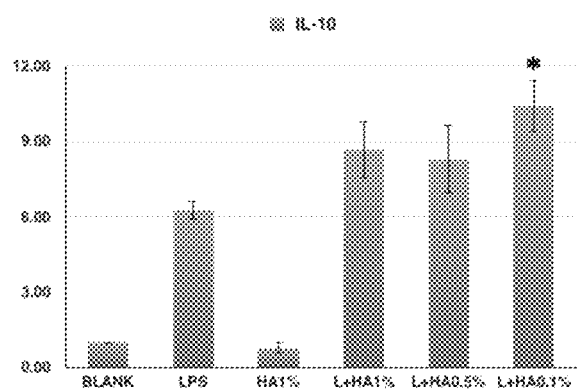

Results: FIG. 3 showed that Injection 1 inhibited the cloning and growth of *Porphyromonas gingivalis*, suggesting that the HA fragment injection was not favorable for the growth of *Porphyromonas gingivalis* (note: the negative control was normal saline, and the positive control was antibiotic metronidazole);

FIG. 4 showed that Injection 1 inhibited the cloning and growth of *Porphyromonas gingivalis* in the in vivo experiment on mice, suggesting that the HA fragment injection was not favorable for the growth of *Porphyromonas gingivalis* at the epidermal wound of small animals;

FIGS. 5A-5E showed that Injection 1 significantly enhanced IL-10 secretion and inhibited the secretions of TNF, IL-1, IL-6 and interferon beta, which were induced by endotoxin (LPS), of human TLR4 receptor positive cells. The results of Injection 2 (data not shown) were similar to the above results.

Conclusion:

2. The above HA fragment injections (Injection 1 and Injection 2) have significant anti-inflammatory effect on in-vitro cultured human cells, and one of the main mechanisms of action may be that it accelerates the secretion of the anti-inflammatory cytokine IL-10, suggesting that B-HA is different from common HA. Although it has the same chemical composition of HA, it may combine with TLR4 by its different 3-dimensional molecular arrangements so as to antagonize endotoxin, accelerate the secretion of the anti-inflammatory cytokine IL-10, and to realize the actions of anti-inflammation, including relieving pain and itching, and effectively treating various diseases and morbid states; of course, some studies (including: Cuixia Yang, Manlin Cao, Hua Liu, Yiqing He, Jing Xu, Yan Du, Yiwen Liu, Wenjuan Wang, Lian Cui, Jiajie Hu, Feng Gao, The high and low molecular weight forms of hyaluronan have distinct effects on CD44 Clustering, Published on Nov. 1, 2012 as Manuscript M112.349209) also suggested that the therapeutic mechanism of HA fragments may also be involved in the regulation of inflammatory cell migration into inflamed tissues which is mediated by CD44 receptor. This is a new action mechanism of LMW-HA fragments for treating various diseases and morbid states, as well as serves as an activity assay for detection of B-HA anti-inflammation bioactivity.

2. The above HA fragment injections (Injection 1 and injection 2) have bacterial growth inhibiting or antimicrobial activities both in vivo and in vitro.

Embodiment 3

Background: The research in Embodiment 2 indicates that B-HA may realize the actions of anti-inflammation, relieving pain and itching, and effectively treating various diseases and morbid states by a new action mechanism of accelerating the secretion of anti-inflammatory cytokine IL-10 through interaction with TLR4. The action mechanism provides a theoretical foundation for B-HA in the unexpectedly effective treatment of various diseases and morbid states.

Objective: To study the effects of the above I-HA fragment injections (Injection 1 and Injection 2) on inflammation in small animals and large animals.

Research Background: Research literatures show that the bioactivity or function of HA or its fragments is not only related to the molecular weight and/or the manufacture method, but also to the species of animals. The studies in small animals such as mice suggest that the bioactivity of HA fragments (LMW-HA) promotes inflammations, but the studies in large animals and human suggest that the bioactivity of HA inhibits inflammations. Therefore, different species of animals including small and large are employed in this embodiment to study the bioactivity of the above HA fragment injections (Injection 1 and Injection 2) on different types of inflammation. The results demonstrated that HA fragment injection has an anti-inflammatory activity in large animals.

3.1 Bioactivity of HA Fragment Injection (B-HA) in Inflammatory Cervical Wound, Spinal Cord Wound and Axonal Sprouting of Small Animal Mice.

A total of 10 female ICR mice were used in this experiment. Dissect the cervical spinal cord and cut it off with a 11 #scalpel. Protect the cut spinal cord wounds with PEG MW 400 cell membrane fusogen, then suture the muscle and skin, and provide nutrition via caudal veins of the mice 4 times a day using venous high-nutrient normal saline and HA fragment injection+venous high-nutrient normal saline. After 4 weeks postoperatively, all the mice had partial neurobehavioral recovery, and then all the mice were killed. Cryopreserve the cut spinal cord wounds using dry ice and perform cryosection, then fix them with 4% formalin and perform immunohistochemical staining using Anti-neurofilament 200 and DAPI, and examine axonal sprouting using a fluorescent or confocal microscope.

Results: Table 1 showed the inflammations of cervical wounds, the axonal sprouting on the surface and the wound healing of spinal cord wound in the mice treated by the above HA fragment Injection 1 and control mice. The situations of Injection 2 were basically the same as those of Injection 1 without significant differences, and those was not shown here.

TABLE 1

Inflammations of Cervical Wound, Axonal Budding on the Surface of Spinal Cord Wound and Wound Healing in the Mice

| | Number of Samples | Axonal Sprouting on the Surface of Spinal Cord Wound | Control Conditions of Inflammations of Wound | Wound Healing |
|---|---|---|---|---|
| Venous High Nutrition + Normal Saline | 5 | + | + | + |
| 1% B-HA + Venous High Nutrition + Normal Saline | 5 | + | + | + |

Note:
Axonal sprouting on the surface of spinal cord wound was judged as −, + and ++, representing no sprouting, sprouting and obvious sprouting, respectively; the control conditions of inflammations of wound were judged as −, + and ++, representing that the inflammation was poorly controlled, properly controlled and perfectly controlled, respectively; wound healing was judgd as −, + and ++, representing that the wound healing was quite abnormal, normal, and obviously better than normal, respectively.

Conclusion: The above HA fragment injections (Injection 1 and Injection 2) cannot significantly control the inflammation of cervical wound and cannot significantly promote the axonal sprouting and wound healing of spinal cord wound in mice, indicating that the HA fragment injections have no obvious anti-inflammatory effect on mice as a species of small animals.

3.2. A Study of Controlling Myocardial Inflammation in Mice.

Ten C57/BL6 mice of age 6-week were used in this experiment, and mice models of myocardial inflammation were produced using angiotensin II (1,500 ng/kg per minute) for 7 consecutive days. With 5 mice in each group, Group 1 was injected with HA fragment injection+normal saline, and Group 2 was injected with normal saline. After 7 days, heart sections were stained with hematoxylin, eosin and Masson trichrome for histochemical staining to observe the infiltration of myocardial inflammatory cells.

Results: Table 2 showed the effect of HA fragment Injection 1 and normal saline on the myocardial infiltration of inflammatory cells of the mice. The effect of Injection 2 were basically the same as those of Injection 1 without significant differences, and those were not shown here.

TABLE 2

Myocardial Infiltration of Inflammatory Cells in Mice

| | Number of Samples | Infiltration of Inflammatory Cells |
|---|---|---|
| Normal Saline | 5 | + |
| 1% B-HA + Normal Saline | 5 | ++ |

Note:
The myocardial infiltration of inflammatory cells was judged as −, + and ++, representing that the infiltration of inflammatory cells was not obvious, obvious and quite obvious, respectively.

Conclusion: The above HA fragment injections (Injection 1 and Injection 2) significantly promote the infiltration of myocardial inflammatory cells induced by angiotensin 11 in mice, indicating that the HA fragment injections have the bioactivity in promoting inflammation in mice as a species of small animals.

3.3 Bioactivity of B-HA (HA Fragment Injection 1) on Abdominal Adhesion in Dogs.

Six healthy beagle dogs were used in this experiment, weighing 6.8±0.8 kg. After 7 days of pre-feeding, the 6 dogs were randomly divided into blank control group (n=2), B-HA low-dose group (n=2) and B-HA high-dose group (n=2). The experimental dogs were fasted for 12 h and deprived of water for 6 h before operation. At 15 min before operation, the dogs in the high-dose group were subcutaneously injected with the above HA fragment injection 0.8 ml/kg on the back; the dogs in the low-dose group were subcutaneously injected with the above HA fragment injection 0.4 ml/kg on the back; the dogs in the blank group were not injected. Perform anesthetization and conventional preparation of operative site, and fix them in a supine position, conventionally open the abdominal cavity along the midline of abdomen at 2 cm behind the umbilicus, search the cecum and find the ileocecal junction, take the ileum at about 20 cm from the ileocecal junction out of the abdominal cavity, isolate and conventionally cut off the intestinal canal, and perform end-to-end anastomosis in a full-thickness continuous suture. On completion of suturing, inject normal saline into the anastomotic part, check the airtightness of the anastomotic part, apply 2 ml of the above HA fragment injection at the operative site in the low-dose group and the high-dose group, and then suture the abdominal wall layer by layer. Record the operative practice in details during the operation. The dogs were fasted for 3 days and were then given a liquid diet (adding appropriate oral liquid in yogurt for salt supplementation) with increasing amounts, the animals were fed with soft dog food after defecation and gradually transited to normal dog food, and postoperative observation was performed every morning for 7 consecutive days.

Results: 1. Postoperative observation: The postoperative conditions of the dogs were observed, and it was found that in the untreated blank group, the mental state and activity state were significantly worse than those in the experimental groups within 2 days postoperatively, fever occurred within 4 days postoperatively, and the body temperature, mental state and activity state recovered to the preoperative levels from Day 5 postoperatively to the end of monitoring; 2. In the HA fragment injection low-dose and high-dose groups, the postoperative mental state and activity state were not significantly different from those postoperatively, indicating that the HA fragment injection effectively controlled the postoperative fever, abdominal inflammation and pain induced by system inflammatory factors, it did not affect the activity and promoted the recovery of intestinal peristalsis, and it reduced the possibility of abdominal adhesion; 3. At Day 7 postoperatively, exploratory laparotomy was performed in each group, there was no wound healing disorder by visual inspection, such as intestinal anastomotic fistula and intestinal stenosis or obstruction. In the blank group, the adhesion of operative site with greater momentum was observed. In the HA fragment injection low-dose and high-dose groups in Embodiment 1, the adhesion of operative site with greater momentum was not observed. Local adhesion of surgically wounded site with adjacent intestinal tract could be observed in all the blank group and the HA fragment injection low-dose and high-dose groups, and it was speculated that the local adhesion of surgically wounded site with adjacent intestinal tract could be effectively obstructed by the gel physical method of high-viscosity HA fragment.

TABLE 3

Experimental Results of HA Fragment Injection 1 in Preventing and Treating Abdominal Adhesions of Dogs.

| | Number of samples | Postoperative body temperature, mental state and activity state | Adhesion of intestinal anastomotic stoma with greater omentum | Post-operative wound healing disorder |
|---|---|---|---|---|
| Blank Group (untreated) | 2 | Obviously poor mental state, inactivity, high fever as compared with those preoperatively | Yes | No |
| Low-dose HA Fragment Injection | 2 | No significant difference in body temperature, mental state and activity state as compared with those preoperatively | No | No |
| High-dose HA Fragment Injection | 2 | No significant difference in body temperature, mental state and activity state as compared with those preoperatively | No | No |

Conclusion: The subcutaneous injection of HA fragment injection (Injection 1) and administration by applying on the operative site can significantly improve fever, abdominal inflammation and pain induced by released systemic inflammation factors after intestinal anastomosis operation in dogs. Besides, these therapeutic actions do not affect physical activities and promote the recovery of intestinal peristalsis, and reduce possible abdominal adhesion. In addition, side effects including wound healing disorders are not observed, such as intestinal anastomotic fistula and intestinal stenosis or obstruction. Results indicate that the above HA fragment injections play a role in preventing and treating local abdominal adhesions by their anti-inflammatory action in dogs as a species of large animals.

3.4. Effect of HA Fragment Injections in Controlling Skin Wound Inflammation in Dogs.

Six healthy beagle dogs were used, weighing 6.8±0.8 kg. After 7 days of pre-feeding, the 6 dogs were randomly divided into blank control group (n=3) and HA fragment injection treatment groups (n=3). The experimental dogs were fasted for 12 h and deprived of water for 6 h preoperatively. At 15 min preoperatively, the dogs in the HA fragment Injection 1 treatment group 1 and the HA fragment injection 2 treatment group 2 were injected subcutaneously with 0.8%/kg normal saline containing 1% B-HA, and those in the blank group were injected subcutaneously with normal saline. Perform anesthesia and conventional preparation of operative site, incise for 3 cm on both sides of the midline on the back without suture, and contaminate the wound with contaminated soil. After operation, the dogs in the treatment groups 1 and 2 were injected subcutaneously with 0.8 ml/kg HA fragment injection normal saline on the back every day, whereas those in the blank group were injected subcutaneously with normal saline on the back every day, and postoperative observation was performed every morning for 7 consecutive days.

Results: See Table 4.

TABLE 4

Effect of HA Fragment Injections in the Back Wound Inflammation of Dogs.

| | Number of samples | Period of inflammation (days) | Situation of back wound inflamemation | Size of back wound after incrustation |
|---|---|---|---|---|
| HA Fragment Injection 1 Experimental Group 1 | 3 | 5 | Quite unobvious | Small |
| HA Fragment Injection 2 Experimental Group 2 | 3 | 5 | Quite unobvious | Small |
| Normal Saline Control Group | 3 | 10 | Quite obvious | Large |

By the postoperative observation for 1~7 days, the inflammation and healing of back wounds of the dogs in the HA fragment injection treatment groups 1, 2 were significantly better than those in the normal saline treatment group.

Conclusion: The subcutaneous injection of HA fragment injections effectively controls the back wound inflammation of the dogs and promotes the back wound healing of the dogs, indicating that the HA fragment injections have an anti-inflammatory effect on dogs as a species of large animals.

3.5. A Study of Controlling Oral Wound Inflammation in Cats.

15 pet cats with oral wound inflammation were selected from a pet hospital, 5 cats were treated by local injection of 50 mg of HA fragment Injection 1 (treatment group 1), 5 cats were treated by local injection of 50 mg of HA fragment Injection 2 (treatment group 2), once a day for 3 consecutive days, and the therapeutic effect was observed every morning. The other 5 pet cats with oral wound inflammation from the pet hospital were not treated as the control group.

Results: See Table 5.

TABLE 5

Results of Oral Wound Inflammation of the Cats Treated by HA Fragment Injections.

| | Number of samples | Redness and swelling of oral wound at Day 1 after treatment | Redness and swelling of oral wound at Day 3 after treatment |
|---|---|---|---|
| HA Fragment Injection 1 Treatment Group 1 | 5 | Obviously alleviated | Almost disappear |
| HA Fragment Injection 2 Treatment Group 2 | 5 | Obviously alleviated | Almost disappear |
| Control Group (untreated) | 5 | Not alleviated | Not alleviated |

The observation at Day 1~3 after the treatment with HA fragment injections showed that the local injection of HA fragment injection 1 or injection 2 significantly controlled the redness and swelling of wound as the oral wound inflammation of the pet cats, and had a rapid anti-inflammatory effect on wound.

Conclusion: The HA fragment injections have a rapid anti-inflammatory effect on the oral wound inflammation of pet cats, and can significantly control the redness, swelling and pain of wounds, indicating that the HA fragment injections have an anti-inflammatory effect on cats.

6. A Study of Controlling Inflammatory Cough in Cows.

Seven cows with inflammatory cough received by a veterinary hospital were treated by subcutaneous injection of 1 g of HA fragment Injection 1, once a day for 3 consecutive days, and the therapeutic effect was observed every morning. Another 7 cows with inflammatory cough received by the veterinary hospital were not treated as the control group.

Results: See Table 6.

TABLE 6

Therapeutic Effect of HA Fragment Injection 1 on Inflammatory Cough in Cows.

| | Number of samples | Cough at Day 1 after treatment | Cough at Day 3 after treatment |
|---|---|---|---|
| HA fragment Injection 1 Treatment Group | 7 | Obviously alleviated | Almost disappear |
| Control Group (untreated) | 7 | Not alleviated | Not alleviated |

The observation at Day 1~3 after treatment with HA fragment Injection 1 showed that the inflammatory cough of the cows could be controlled at 3 hours after subcutaneous injection of 1 g of HA fragment Injection 1, and it could be completely cured after 3 days of treatment.

Conclusion: The HA fragment injection is effective in treating inflammatory cough in cows, indicating that the HA fragment injection has an anti-inflammatory effect on cows as a species of large animals.

3.7 Experiment of Controlling Arthritis in Horses.

Seven horses with arthritis received by a veterinary hospital were treated by subcutaneous injection of 1 g of HA fragment Injection 1, once a day for 3 consecutive days, and the therapeutic effect was observed every morning.

Results: See Table

TABLE 7

Therapeutic Effect of HA Fragment Injection 1 on Arthritis Pain in Horses.

| | Number of samples | Walking abnormalities caused by arthritis pain at Day 1 after treatment | Walking abnormalities caused by arthritis pain at Day 3 after treatment |
|---|---|---|---|
| HA fragment Injection 1 Treatment Group | 7 | Begin to alleviate | Obviously alleviated |
| Control Group (untreated) | 7 | Not alleviated | Not alleviated |

At Day 1~3 after treatment with HA fragment Injection 1, the observation on walking abnormalities caused by arthritis pain showed that the walking abnormalities caused by arthritis pain in the horses were significantly alleviated at Day 1 after subcutaneous injection of 1 g of HA fragment Injection 1, and the effect was more significant after 3 days of treatment.

Conclusion: The HA fragment injection is effective in treating arthritis pain of horses as large animals, indicating that the HA fragment injection has an anti-inflammatory effect on hoses as a species of large animals.

Summary on the researches in Embodiment 3: According to the research results in Embodiment 3, the research results of the function of LMW-HA fragments are completely different in mice and large animals, and thus it is predicted that the research results of the function of LMW-HA fragments in humans may be completely different from those in mice.

Embodiment 4

Research Background: According to the above researches in Embodiment 3, some researches on function of HA or its fragments using mice described in previous references cannot represent the research results on function of HA or its fragments in large animals and human, and the above LMW-HA fragment injections have "unexpected" different functions for human.

Objective: To study the anti-aging effect and safety of Injection 1 or B-HA injection (experiment group 1) containing protein residue of recombinant human hyaluronidase PH20 and injection 2 (experimental group 2) not containing protein residue of recombinant human hyaluronidase PH20 in the above Embodiment 1 on human facial cosmetology.

Methods: The HA fragment injection containing protein residue of recombinant human hyaluronidase PH20, i.e., HA fragment injection 1 (B-HA injection) in Embodiment 1, was used as the experimental group 1 to carry out a clinical study among 98 subjects (with the mean age of 62±18 years, 50 males and 48 females) with various diseases, subclinical problems or aging and aging-related diseases in current China's environment of air pollution, drinking water pollution and work stress; the HA fragment injection not containing protein residue of recombinant human hyaluronidase PH20, i.e., HA fragment Injection 2 in Embodiment 1, was used as the experimental group 2 to carry out a clinical study among 100 subjects (with the mean age of 61±20 years, 49 males and 51 females) with various diseases or subclinical problems in current China's environment of air pollution, drinking water pollution and work stress or aging and aging-related diseases; they were injected with 100 mg (it refers to 100 mg of HA fragments with a molecular weight distribution of 10 KD-60 KD contained in the injection, the same below) via abdominal subcutaneous fat layer, 12 times a day for at least 7 consecutive days;

The cosmetic effects of the two injections (1 and 2) were compared by observing the facial features or pictures of the subjects before and after treatment (score: ineffective, undetermined, obviously effective), and the safety of the injection was evaluated by means of doctor's inquiry about the subject's feeling, symptoms, physical examination and laboratory tests, namely, whether there were side effects or not, including pain at the injection site, physical discomfort before and after injection, mental state and physical strength, and changes in original physical pain, original physical diseases and various original subclinical problems.

Results: See Table 8.

TABLE 8

Effect of the Two Injections (1 and 2) on Facial Cosmetology and Anti-aging.

|  | Ineffective | Undetermined | Obviously effective | Number of samples |
|---|---|---|---|---|
| Experimental Group 1 (Injection 1) | 0 | 0 | 98 | 98 |
| Experimental Group 2 (Injection 2) | 0 | 0 | 100 | 100 |

Note:
Self-control was employed in this study, which refers to the comparison between the subject's current state (after treatment) and the state of a period before treatment.

Figure 7:
FIG. 7 shows the comparison of pictures of partial subjects before and after the treatment with injection of LMW-HA fragments via abdominal subcutaneous fat layer, indicating that the injection of LMW-HA fragments has a therapeutic effect on human facial cosmetology and facial anti-aging.

FIG. 7 showed the comparison in the photos of some subjects before and after treatment, as well as the therapeutic effect of the HA fragment injections on human facial cosmetology and facial aging, it also indicated that the HA fragment injections via abdominal subcutaneous fat layer significantly reduced the thickness of subcutaneous fat tissue in head, face, neck, shoulders, back, abdomen and upper and lower limbs.

TABLE 9

Effect of the Two Injections on Reducing Subcutaneous Fat.

|  | Ineffective | Undetermined | Obviously effective | Number of samples |
|---|---|---|---|---|
| Experimental Group 1 (Injection 1) | 6 | 18 | 74 | 98 |
| Experimental Group 2 (Injection 2) | 3 | 18 | 79 | 100 |

Note:
Self-control was employed in this study, which refers to the comparison between the subject's current state (after treatment) the state of a period before treatment.

TABLE 10

Existence of Pain, Local Redness and Swelling, Local and Systemic Allergy After Deep Injection of the Two Injections via Abdominal Subcutaneous Fat Layer.

|  | No | Undetermined | Yes | Number of samples |
|---|---|---|---|---|
| Experimental Group 1 (Injection 1) | 98 | 0 | 0 | 98 |
| Experimental Group 2 (Injection 2) | 100 | 0 | 0 | 100 |

In addition to the above cosmetic effects, safety and side effects, it was also found that 9 cases felt comfortable and short period of sleepy after injection via abdominal subcutaneous fat layer; the sleepiness lasted for 0.5~1.5 h, wherein, 3 cases slept for 1.0 h after the first injection, and the energy and physical strength enhanced significantly after waking up; the other 6 cases did not feel sleepy any more after injection for twice.

TABLE 11

Side effect of Sleepiness After Both Injections.

|  | No | Undetermined | Yes | Number of samples |
|---|---|---|---|---|
| Experimental Group 1 (Injection 1) | 92 | 0 | 6 | 98 |
| Experimental Group 2 (Injection 2) | 97 | 0 | 3 | 100 |

Unexpectedly, 185 of all the 198 subjects felt an enhancement in energy and physical strength at 30 min after injection via abdominal subcutaneous fat layer, demonstrated by the desire to talk, wash dishes, cook, walk, plan to travel, work and no desire to rest, etc., which lasted for 3~4 days.

TABLE 12

Effect on Enhancing Energy and Physical Strength After Both Injections.

|  | No | Undetermined | Obvious | Number of samples |
|---|---|---|---|---|
| Experimental Group 1 (Injection I) | 0 | 8 | 90 | 98 |
| Experimental Group 2 (injection 2) | 0 | 5 | 95 | 100 |

Note:
Self-control was employed in this study, which refers to the comparison between the subject's current state (after treatment) the state of a period before treatment.

77 of the 198 subjects (including 98 cases in the experimental group 1 and 100 cases in the experimental group 2) suffered from different pains in shoulders, back, waist, legs and arm, and unexpectedly, they all felt that the pains were relieved at 30 min after injection via abdominal subcutaneous fat layer. Among them, 27 cases were additionally injected with 50 mg at the local painful site, and the pain began to relieve at 2 min after the injection, which was equivalent to the effect of the previous anesthesia treatment by local injection of lidocaine combined with prednisone complained by 12 cases.

TABLE 13

Analgesic Effects of the Two Injections (Note: mixed clinical data of Injection 1 and 2)

|  | Pain began to relieve within 30 min after the first injection | Pain disappeared after injection treatment (15 × 100 mg) without relapse within 60 days | Pain disappeared after injection treatment (15 × 100 mg) without relapse within 6 months or more | Number of Samples |
|---|---|---|---|---|
| Myofascitis in waist, back, neck and upper and lower limbs | 17 | 20 | 16 | 21 |
| Hyperosteogeny and bone spur in waist, back and neck | 20 | 26 | 16 | 30 |
| Old sports injury | 8 | 14 | 6 | 12 |
| Aging related or unknown reasons | 12 | 14 | 8 | 14 |

Note:
Self-control was employed in this study, which refers to the comparison between the subject's current state (after treatment) the state of a period before treatment.

83 of the 198 subjects (including 98 cases in the experimental group 1 and 100 cases in the experimental group 2) suffered from itching of different degrees, and unexpectedly, they all felt that the itching was relieved or disappeared at Day 1 after injection via abdominal subcutaneous fat layer.

TABLE 14

Antipruritic Effect of the Two Injections (Note: mixed clincal data of Injection 1 and 2).

|  | Itching began to relieve within 1 day after the first injection | Itching did not relapse within 7 days after injection treatment (15 × 100 mg) | Itching did not relapse within 60 days after injection treatment (15 × 100 mg) | Number of samples |
|---|---|---|---|---|
| Neurodermatitis | 15 | 13 | 12 | 16 |
| Psoriasis | 26 | 26 | 22 | 26 |
| Senile Eczema | 24 | 24 | 20 | 24 |
| Skin Scar Inflammation and Hyperplasia | 9 | 9 | 6 | 9 |
| Unknown reasons | 8 | 8 | 7 | 8 |

Note:
Self-control was employed in this study, which refers to the comparison between the subject's current state (after treatment) and the state of a period before treatment.

Conclusions:
1. Both HA fragment injections (Injection 1 and Injection 2) containing and not containing protein residue of recombinant human hyaluronidase have an effect on human facial cosmetology and facial anti-aging.
2. Both HA fragment injections (Injection 1 and Injection 2) containing and not containing protein residue of recombinant human hyaluronidase significantly reduce the thickness of subcutaneous fat tissue in head, face, neck, shoulders, back, abdomen and upper and lower limbs.
3. Pain, local redness and swelling, as well as local and systemic allergy are not observed after both HA fragment injections (Injection 1 and Injection 2) containing and not containing protein residue of recombinant human hyaluronidase were injected via abdominal subcutaneous fat layer. It is convenient to use.
4. After the first injection of both HA fragment injections (Injection 1 and Injection 2) containing and not containing protein residue of recombinant human hyaluronidase via abdominal subcutaneous fat layer, the subjects feel comfortable and sleepy and want to sleep, with an incidence rate less than 4.0%.
5. Unexpectedly, both HA fragment injections (Injection 1 and Injection 2) containing and not containing protein residue of recombinant human hyaluronidase injected via abdominal subcutaneous fat layer have an effect of significantly enhancing energy and physical strength.
6. Unexpectedly, both HA fragment injections (Injection 1 and Injection 2) containing and not containing protein residue of recombinant human hyaluronidase injected via abdominal subcutaneous fat layer have a rapid and significant analgesic (pain-relieving) effect.
7. Unexpectedly, both HA fragment injections (Injection 1 and Injection 2) containing and not containing protein residue of recombinant human hyaluronidase injected via abdominal subcutaneous fat layer have an significant antipruritic effect.
8. The above experimental results suggest that both HA fragment injections of Injection 1 and Injection 2 in Embodiment 1 are the equivalent HA fragment injections of the same kind, that is, 100 mg of HA fragment injection with the same active ingredient of the same amount.

Embodiment 5

Objective: To further analyze the changes in the diseases and subclinical problems of the 198 subjects before and after treatment with HA fragment injections in "Embodiment 4", and to identify the new clinical indications of myofascitis and old sports injuries of the HA fragment injections (Injection 1 and Injection 2).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indications of myofascitis and old sports injuries.

Results:

Rapid and effective treatment for myofascitis and old sports injuries: Myofascitis and old sports injuries are diseases related to sports injuries and senile degeneration, and the pathogenesis is not fully clear. There are professional chiropractors specialized in treating these diseases in the United States, whereas there is still no curative method at present.

Among the 198 subjects, we analyzed 12 cases of myofascitis in waist, back, neck and upper and lower limbs (6 cases in the experimental group 1 and 6 cases in the experimental group 2) and 14 cases of old sports injuries (6 cases in the experimental group 1 and 8 cases in the experimental group 2), and the results were as shown in Table 15:

TABLE 15

Therapeutic Effect of HA Fragment Injections on Myofascitis and Old Sports Injuries

|  | Pain began to relieve within 30 min after the first injection | Pain disappeared after injection treatment (15 × 100 mg) without relapse within 60 days | Pain disappeared after injection treatment (15 × 100 mg) without relapse within 12 months or more | Number of samples |
|---|---|---|---|---|
| Myofascitis in Waist, Back, Neck and Upper and Lower Limbs | 12 | 12 | 8 | 12 |
| Old Sports Injuries | 12 | 14 | 10 | 14 |

Note:
Self-control was employed in this study, which refers to the comparison between the subject's current state (after treatment) the state of a period before treatment.

Among them, a 57-year-old male subject had suffered from myofascitis for 3 years due to old sports injury for 17 years. It attacked when days became cold every year, the pain was very afflicting, and certain muscular movements may also cause the pain, and the range of activity was limited for neck and back. The pain was relieved at 30 min after injection of 100 mg via abdominal subcutaneous fat layer, and then the effect was better by additional deep injection of 100 mg at the local pain points of neck and back. After 15×100 mg of injections within 2 months, the pain point and nodule on the back disappeared, and the thickness of neck and back muscles became thinner, without relapse within 12 months. The results showed that in addition to pain relief, the HA fragment injections finally solved the old sports injury and inflammatory lesions of myofascitis, realizing the purpose of recombination and regeneration of muscles and muscular fasciae.

Conclusion: The HA fragment injection via abdominal subcutaneous fat layer or at pain point or diseased site effectively treats painful myofascitis as well as muscle and tendon injuries in waist, back, neck and shoulders.

Embodiment 6

Objective: To further analyze the changes in the diseases and subclinical problems of the 198 subjects before and after treatment with HA fragment injections in "Embodiment 4", and to identify the new clinical indications of bone spur and the protrusion of intervertebral disc or diseases of lumbar spinal diseases and cervical vertebra of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the I-HA fragment injections, so as to identify the therapeutic effect of the HA fragment injections on the new clinical indications of bone spur and the protrusion of intervertebral disc or lumbar spondylosis, back disease and cervical spondylosis.

Results:

HA fragment injections can achieve rapid and effective treatment of bone spur and the protrusion of intervertebral disc or lumbar spondylosis, back disease and cervical spondylosis. Bone spur and the protrusion of intervertebral disc or lumbar spondylosis, back disease and cervical spondylosis are diseases related to senile degeneration and sports injuries, the pathogenesis is not fully clear, and there is still no curative method at present. Among the 198 subjects, we analyzed 30 cases of hyperosteogeny and bone spur in waist, back and neck (17 cases in the experimental group 1 and 13 cases in the experimental group 2), and the results were as shown in Table 16:

TABLE 16

Therapeutic Effect of HA Fragment Injections on the Protrusion of Intervertebral Disc or Lumbar Spondylosis, Back Disease and Cervical Spondylosis.

| | Pain began to relieve within 30 min after the first injection | Pain disappeared after injection treatment (15 × 100 mg) without relapse within 60 days | Pain disappeared after injection treatment (15 × 100 mg) without relapse within 6 months or more | Number of samples |
|---|---|---|---|---|
| Hyperosteogeny and Bone Spur in Waist, Back and Neck | 26 | 30 | 23 | 30 |

Note:
Self-control was employed in this study, which refers to the comparison between the subject's current state (after treatment) the state of a period before treatment.

Among them, a 57-year-old female subject suffered from hyperosteogeny and bone spur in waist, back and neck for 14 years. It attacked occasionally with very afflicting pain, which may also by caused by certain muscular movements. The range of activity was limited for neck and back, accompanied by the numbness of upper limbs and descending working ability. After injection of 100 mg via abdominal subcutaneous fat layer on Day 1, the subject complained that the pain was relieved by more than 50%, and she could make dumplings and cook in the kitchen; after injection of 100 mg on Day 2, the subject complained that the pain was relieved by more than 80%; and after injection of 100 mg on Day 3, the subject complained that the pain was relieved by more than 95%. After 15×100 mg of injections within 2 months, it did not relapse any more. The results showed that in addition to pain relief, the HA fragment injections finally started the recombination and regeneration of the inflammatory lesions of old sports injury.

Among them, another 57-year-old female subject suffered from hyperosteogeny and bone spur in neck for 4 years. The range of activity was limited for neck and back. It attacked occasionally with afflicting pain and was accompanied by the feeling of facial numbness, and certain muscular movements may also cause the pain, accompanied by the numbness of upper limbs and descending working ability. After injection of 100 mg via abdominal subcutaneous fat layer on Day 1, the subject complained that the pain was relieved by more than 50%; and after injection of 100 mg on Day 2, the subject complained that the pain was relieved by more than 80%. After 15×100 mg of injections within 2 months, it did not relapse any more. The results showed that in addition to pain relief, the HA fragment injections also started the recombination and regeneration of the inflammatory lesions of old sports injury. Note: All of the above subjects continued the treatment for more than 6 months to wait for the result of relapse or not.

Among them, another 74-year-old male subject suffered from combined lumbar spondylosis, back disease and cervical spondylosis for 20 years. The pain was afflicting and accompanied by movement disorders, and he prepared to hospitalize for operation. He was injected with the HA fragment injection via abdominal subcutaneous fat layer for 60×100 mg within 8 months, and he could walk and swim without pain, indicating that the conservative non-surgical treatment was successful; it also suggested that the HA fragment injection could finally cure the inflammatory lesions of old sports injury and promote the recombination and regeneration of tissues.

Conclusion: The HA fragment injections via abdominal subcutaneous fat layer or at pain point or at diseased site is used for effectively treating the painful hyperosteogeny, bone spur, the protrusion of intervertebral disc, and the lumbar spondylosis, back disease and cervical spondylosis.

Embodiment 7

Objective: To further analyze the changes in the diseases and subclinical problems of the 198 subjects before and after treatment with HA fragment injections in "Embodiment 4", and to identify the new clinical indications of vitreous opacity and vitreous detachment of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indications of vitreous opacity and vitreous detachment.

Results:

HA fragment injection in rapid and effective treatment of vitreous opacity: Vitreous opacity is a senile degenerative disease, the pathogenesis of which is not fully clear, and there is still no curative method at present. Vitreous opacity also known as muscae volitantes will further develop into vitreous detachment that impairs the fundus and affects the vision. Among the 198 subjects, we analyzed 19 cases of vitreous opacity and vitreous detachment (11 cases in the experimental group 1 and 8 cases in the experimental group 2), and the results were as shown in Table 17:

TABLE 17

Therapeutic Effect of HA Fragment Injections on Vitreous Opacity and Vitreous Detachment.

|  | Unilateral or bilateral spots of muscae volitantes began to relieve, dissipate and disappear within 3 days after the first injection | The unilateral or bilateral spots of muscae volitantes relieved, dissipated and disappeared after injection treatment (15 × 100 mg) without relapse | The vision was significantly ameliorated after 5 × 100 mg injection | Number of Samples |
|---|---|---|---|---|
| Vitreous Opacity (Muscae Volitantes) or Vitreous Detachment | 19 | 19 | 9 | 19 |

Note:
Self-control was employed in this study, which refers to the comparison between the subject's current state (after treatment) the state of a period before treatment.

Figure 6:
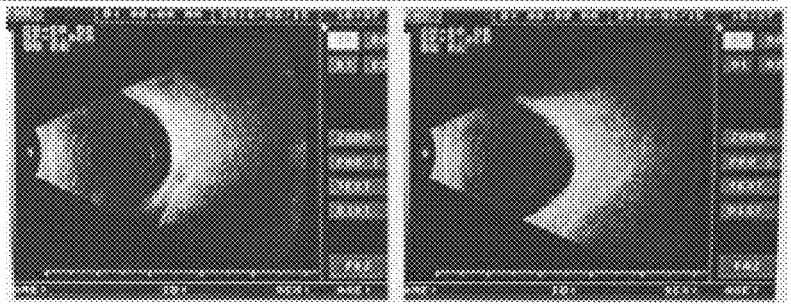
FIG. 6 shows the ophthalmological laboratory diagnostic result of a subject suffering from vitreous opacity and vitreous detachment.

A 61-year-old female subject was treated by 100 mg of HA fragment injection via abdominal subcutaneous fat layer for the need of facial cosmetic treatment, and FIG. 6 showed the laboratory diagnosis of the subject with vitreous opacity and vitreous detachment. After injection, it was occasionally found that the vision was ameliorated on Day 2, and the spots of muscae volitantes for eyes became smaller on Day 3; she was injected with 15×100 mg every 3 days continuously. The vision kept ameliorating (from 0.2 to 0.5) and the spots of muscae volitantes became thinner and lighter continuously, without obvious relapse within 2 months. The results showed that the HA fragment injection could rapidly and effectively treat vitreous opacity (muscae volitantes) and vitreous detachment surprisingly.

Conclusion: The HA fragment injections via abdominal subcutaneous fat layer are used for effectively treating muscae volitantesor vitreous opacity and the vitreous detachment and diminution of vision induced by them.

Embodiment 8

Objective: To further analyze the changes in the diseases and subclinical problems of the 198 subjects before and after treatment with HA fragment injections in "Embodiment 4", and to identify the new clinical indication of wound scars with itching (chronic inflammation) and pain (inflammatory pain) of the I-HA fragment injections (I-A fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of wound scars with itching (chronic inflammation) and pain (inflammatory pain).

Results:

HA fragment injections in the treatment of wound scars with itching (chronic inflammation) and pain (inflammatory pain): The small wounds of people with scar diathesis can gradually form large scars and become thickening and itching continuously. The therapeutic targets are to relieve the itching and reduce the scar thickening; the scars formed after extensive burns without skin grafting continue to thicken with itching and chronic inflammation (FIG. 8), and the therapeutic targets are to relieve the itching, eliminate the inflammation and reduce the scar thickening; surgical wounds mainly have redness, pain, inflammatory reactive exudation and secondary infection, and therapeutic targets are to accelerate healing and reduce the scar formation. Among the 198 subjects, we analyzed 14 cases of wound scars with itching (chronic inflammation) and pain (inflammatory pain) (5 cases in the experimental group 1 and 9 cases in the experimental group 2), and the results were as shown in Table 18:

TABLE 18

Therapeutic Effect of HA Fragment Injection on Wound Scars with Itching (Chronic Inflammation) and Pain (Inflammatory Pain).

|  | The itching was relieved, the pain was relieved and the inflammation around scar was relieved after injection of 1 × 100 mg within 1 day | The scar became thinner, the inflammation around scar disappeared, the itching was significantly relieved, and the pain was significantly relieved after injection of 5 × 100 mg | The scar became thinner, and the itching or pain disappeared after injection of 15 × 100 mg | Number of samples |
|---|---|---|---|---|
| Scars of Extensive Burn | 3 | 3 | 0 | 3 |
| Traumatic Scars (Scar Diathesisantibiotics | 5 | 5 | 3 | 5 |

TABLE 18-continued

Therapeutic Effect of HA Fragment Injection on Wound Scars with
Itching (Chronic Inflammation) and Pain (Inflammatory Pain).

|  | The itching was relieved, the pain was relieved and the inflammation around scar was relieved after injection of 1 × 100 mg within 1 day | The scar became thinner, the inflammation around scar disappeared, the itching was significantly relieved, and the pain was significantly relieved after injection of 5 × 100 mg | The scar became thinner, and the itching or pain disappeared after injection of 15 × 100 mg | Number of samples |
|---|---|---|---|---|
| Scars of Surgical Wound | 6 | 6 | 5 | 6 |

Note:
Self-control was employed in this study, which refers to the comparison between the subject's current state (after treatment) the state of a period before treatment.

Figure 8:
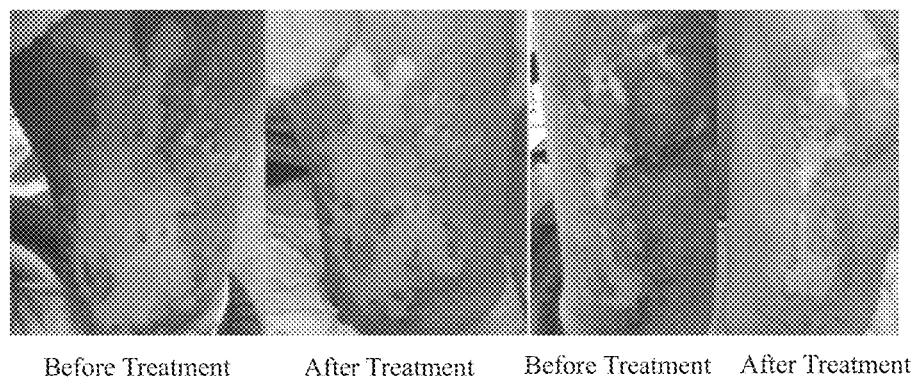
FIG. 8 shows the comparison before and after the treatment with injection of LMW-HA fragments for a case of extensive burns.

A 63-year-old female subject had extensive burns without skin grafting 12 ago. She suffered from serious itching and difficulty in falling asleep, and there were inflammations around the scars. At Day 3 after 2×100 mg HA fragment injections, the scar became thinner, the inflammations around scar disappeared, the itching and the pain was significantly relieved; After 30×100 mg of HA injections continuously, the scar and the peripheral skin were significantly ameliorated, including that the scar became thinner, the inflammations disappeared, and the itching was relieved but did not completely disappear (FIG. 8).

Conclusion: The HA fragment injections via abdominal subcutaneous fat layer are used for effectively treating extensive burns, traumatic scars and scars of surgical wound accompanied by inflammations, itching and pain.

Embodiment 9

Objective: To further analyze the changes in the diseases and subclinical problems of the 198 subjects before and after treatment with HA fragment injections in "Embodiment 4", and to identify the new clinical indication of abdominal mucous membrane adhesion after operation or peritoneal dialysis of the HA fragment injections (HA fragment injections 1 and 2 in Embodiment 1).

Methods: The changes in the diseases and subclinical probles of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of abdominal mucous membrane adhesion after operation or peritoneal dialysis.

Results:

HA fragment injections in rapid and effective treatment of abdominal mucous membrane adhesion after operation or peritoneal dialysis: Surgical injury, abdominal dialysis, etc. can almost cause abdominal mucosal inflammations and adhesions, and can cause symptoms and pathological changes depending on the severity, including abdominal pain, abdominal tenderness, abdominal mass and intestinal obstruction. At present, there is still no feasible way to eradicate abdominal adhesions. Among the 198 subjects, we analyzed 10 cases of abdominal mucous membrane adhesion after operation or dialysis (5 cases in the experimental group 1 and 5 cases in the experimental group 2), and the results were as shown in Table 19:

TABLE 19

HA Fragment Injection in Rapid Treatment of Abdominal
Adhesions After Operation or Peritoneal Dialysis.

|  | Abdominal pain and abdominal tenderness were relieved, and the energy and physical strength began to turn better after 2 × 100 mg injections | Abdominal pain and abdominal tenderness disappeared, and the energy and physical strength significantly turned better after 5 × 100 mg injections | Abdominal mass and intestinal obstruction disappeared after 5 × 100 mg injections | Number of samples |
|---|---|---|---|---|
| Abdominal Adhesions After Operation | 7 | 7 | 7 | 7 |
| Abdominal Adhesions After Peritoneal Dialysis | 3 | 3 | Not applicable | 3 |

Note:
Self-control was employed in this study, which refers to the comparison between the subject's current state (after treatment) the state of a period before treatment.

A 43-year-old female subject began to eat non-liquid food 1 month after subtotal gastrectomy and peripheral lymph node dissection, and then abdominal mass and pain were found. She suffered from vomit after eating, severe weight loss and poor health, and she was clinically diagnosed as intestinal obstruction induced by abdominal adhesions. After 5×100 mg of HA fragment injections via abdominal subcutaneous fat layer, all the above symptoms and signs disappeared, intestinal obstruction did not occur after eating non-liquid food, and the mental state turned better significantly. The therapeutic results suggested that the HA fragment injection eventually eliminated the symptoms and signs of abdominal adhesions may be by reducing the inflammations in abdominal mucosa.

A 43-year-old female subject underwent oophorectomy began to receive 100 mg of HA fragment injection via abdominal subcutaneous fat layer from Day 1 preoperatively, once a day for 5 consecutive days. After the operation, the mental state was obviously better than that after general operations. She could walk on the day of operation, she did not suffer from fever, she had bowel sounds and exhausted on the same day, and the postoperative wound healing was obviously better that that after general operations.

A 53-year-old female subject underwent intestinal anastomosis began to receive 100 mg of HA fragment injection via abdominal subcutaneous fat layer from Day 1 preoperatively, once a day for 7 consecutive days. After the operation, the mental state was obviously better than that after general operations, she could walk slowly by holding the bed on the day of operation, she did not suffer from fever, she had bowel sounds and exhausted on the same day, and the postoperative wound healing was obviously better that that after general operations.

Conclusion: The HA fragment injections via abdominal subcutaneous fat layer or at diseased site can effectively treat pelvic mucous membrane adhesions after operation and peritoneal dialysis, effectively control the inflammatory symptoms caused by operation, obviously accelerate the postoperative rehabilitation and reduce the postoperative pain.

Embodiment 10

Objective: To further analyze the changes in the diseases and subclinical problems of the 198 subjects before and after treatment with HA fragment injections in "Embodiment 4", and to identify the new clinical indication of endometriosis with dysmenorrhea or pelvic mucous membrane adhesion of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of endometriosis with dysmenorrhea or pelvic mucous membrane adhesion.

Results:

HA fragment injections in the treatment of dysmenorrhea or pelvic mucous membrane adhesion: Endometriosis is always accompanied by infertility and dysmenorrhea; infertility and dysmenorrhea may be associated with the inflammation and adhesion of pelvic mucous membrane; there is still no effective method for treating dysmenorrhea and endometriosis or pelvic mucous membrane adhesion; among the 198 subjects, we analyzed 9 cases of pelvic mucous membrane adhesion and dysmenorrhea (4 cases in the experimental group 1 and 5 cases in the experimental group 2), and the results were as shown in Table 20:

TABLE 20

HA Fragment Injection in Treating Endometriosis with Dysmenorrhea or Pelvic Mucous Membrane Adhesion

|  | Dysmenorrhea was significantly relieved after 100 mg injection during the menstruation | Dysmenorrhea almost disappeared after 2 × 100 mg injections during the menstruation | Dysmenorrhea was significantly relieved within 3 months after 15 × 100 mg injections continuously | Number of samples |
|---|---|---|---|---|
| Endometriosis with dysmenorrhea | 9 | 5 | 9 | 9 |

Note:
Self-control was employed in this study, which refers to the comparison between the subject's current state (after treatment) the state of a period before treatment.

A 38-year-old female subject suffered from serious adenomyosis, the ultrasonography showed that the uterus was obviously increased, and dysmenorrheal was very serious. She was injected with 100 mg of HA fragment via abdominal subcutaneous fat layer from the beginning of menstruation, once a day for 3 consecutive days, and the dysmenorrhea was obviously relieved.

A 41-year-old female subject suffered from serious adenomyosis, the ultrasonography showed that the uterus was obviously increased, CA125 was obviously higher than that of normal people, and the dysmenorrhea was serious. She was injected with 100 mg of HA fragment via abdominal subcutaneous fat layer from the beginning of menstruation, once every 2 days for 40 consecutive days, and the dysmenorrhea almost disappeared during two menstruations, CA125 got normal, and ultrasonography showed that the uterus began to reduce.

A 33-year-old female with infertility was found by examination to have endometriosis and ovarian cyst; after the excision by minimally invasive operation, she began to receive 100 mg of HA fragment injection via abdominal subcutaneous fat layer, once every 4 days for 6 consecutive months, and she was pregnant in the $7^{th}$ month.

The above results showed that the HA injections obviously relieved dysmenorrheal, and the HA injections reduced the inflammatory severity of endometriosis in pelvic cavity and the severity of referred pain induced by pelvic adhesion, indicating that the HA fragment injections may also be used for treating infertility caused by poor peristalsis of ovarian ducts induced by endometriosis and pelvic adhesion.

Conclusion: The HA fragment injections via abdominal subcutaneous fat layer are used for effectively controlling dysmenorrhea and effectively treating endometriosis with dysmenorrhea and related diseases.

Embodiment 11

Objective: To further analyze the changes in the diseases and subclinical problems of the 198 subjects before and after treatment with HA fragment injections in "Embodiment 4", and to identify the new clinical indications of itching neurodernmatitis, psoriasis, itching senile eczema, eczema herpeticum or pompholyx of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indications of itching neurodermatitis, psoriasis, itching senile eczema, eczema herpeticum or pompholyx.

Results:

HA fragment injections in the treatment of itching neurodermatitis, psoriasis, itching senile eczema, eczema herpeticum or pompholyx. Among the 198 subjects, we analyzed 29 cases of neurodermatitis, psoriasis, itching senile eczema, eczema herpeticum or pompholyx (14 cases in the experimental group 1 and 15 cases in the experimental group 2), and the results were as shown in Table 21:

TABLE 21

Therapeutic Effect of HA Fragment Injections on Itching Neurodermatitis and Psoriasis.

| | The itching was relieved and the skin inflammation began to vanish within 1 day after 1 × 100 mg injection | The itching was obviously relieved, the skin inflammation vanished, and the skin lesions became thinner after 10 × 100 mg injections | The itching was obviously relieved, the skin inflammation vanished, and the skin lesions disappeared after 20 × 100 mg injections | Number of samples |
|---|---|---|---|---|
| Neurodermatitis | 6 | 6 | 6 | 6 |
| Psoriasis | 7 | 7 | 4 | 7 |

Note:
Self-control was employed in this study, which refers to the comparison between the subject's current state (after treatment) the state of a period before treatment.

Figure 9:
FIG. 9 shows the effect after the treatment with injection of LMW-HA fragments via abdominal subcutaneous fat layer for a case of neurodermatitis (the focus is indicated by arrow in the picture).

In Table 21, 1 subject of neurodermatitis (male, 57 years old) had suffered from neurodermatitis for 8 years, and he had bilateral symmetrical multiple skin lesions, serious itching and local inflammatory skin lesions. The subject was dissatisfied with the therapeutic effect of previous Stelara (anti-IL-12/23 antibody) injection. After 20×100 mg of HA fragment injections via abdominal subcutaneous fat layer, the itching almost disappeared, the inflammatory skin lesions almost recovered (FIG. 9), and the subject was satisfied with the effect.

Figure 10:
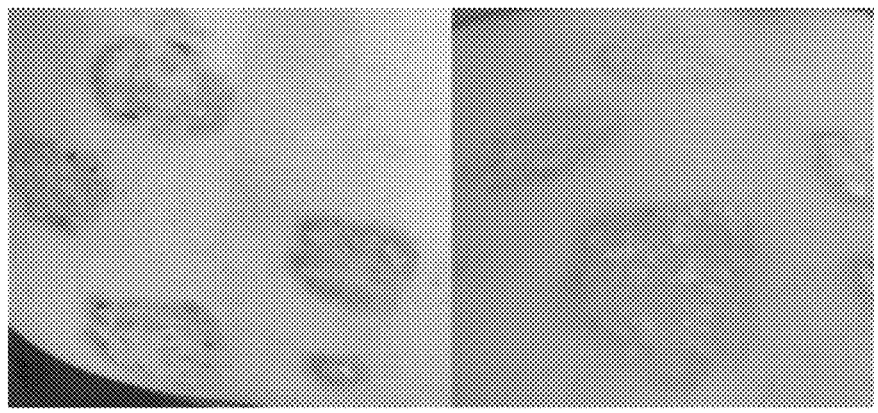
FIG. 10 shows the effect before and after the treatment with injection of LMW-HA fragments via abdominal subcutaneous fat layer for a case of psoriasis.

In Table 21, 1 subject of psoriasis (male, 52 years old) had suffered from psoriasis for 18 years, and he had multiple local inflammatory skin lesions and thickening of skin lesions in abdomen and the upper and lower limbs, accompanied by the itching symptom. The subject was dissatisfied with the therapeutic effect of Stelara (anti-IL-12/23 antibody) injection 2 years ago. After 10×100 mg of HA fragment injections via abdominal subcutaneous fat layer, the itching almost disappeared, the thickened skin lesions obviously became thinner, the inflammatory skin lesions were obviously recovered (FIG. 10), and the subject was satisfied with the effect.

In Table 21, 1 subject of psoriasis (female, 76 years old) had suffered from psoriasis for 48 years, she had multiple local inflammatory skin lesions and thickening of skin lesions in abdomen and the upper and lower limbs, accompanied by the itching symptom, and cortical hormone had not been used. After 20×100 mg of HA fragment injections via abdominal subcutaneous fat layer, the itching disappeared, the skin lesions disappeared completely, and the subject was very satisfied with the effect.

TABLE 22

Therapeutic Effect of HA Fragment Injections on Itching Senile Eczema and Eczema Herpeticum or Pompholyx.

|  | The itching was relieved and the skin inflammation began to vanish within 1 day after 1 × 100 mg injection | The itching disappeared, and the skin lesions almost disappeared after 10 × 100 mg injections | Number of Samples |
|---|---|---|---|
| Senile Eczema | 13 | 13 | 13 |
| Pompholyx | 3 | 3 | 3 |

Note:
Self-control was employed in this study, which refers to the comparison between the subject's current state (after treatment) the state of a period before treatment.

In Table 22, 1 subject of pompholyx (female, 33 years old) had suffered from pompholyx for 9 years, and it attacked every summer. After 20×100 mg of HA fragment injections via abdominal subcutaneous fat layer, pompholyx did not occur during injection and within 1 year after injection.

The results of Tables 21 and 22 showed that the HA fragment injections via abdominal subcutaneous fat layer could treat itching neurodermatitis, psoriasis, itching senile eczema, eczema herpeticum or pompholyx.

Conclusion: The HA fragment injections via abdominal subcutaneous fat layer are used for effectively treating itching neurodermatitis, psoriasis, itching senile eczema and eczema herpeticum or pompholyx.

Embodiment 12

Objective: To further analyze the changes in the diseases and subclinical problems of the 198 subjects before and after treatment with HA fragment injections in "Embodiment 4", and to identify the new clinical indications of senility-related diseases of the HA fragment injections (HA fragment Injections 1 and 2 in Embodiment 1), including periodontal inflammation, dental ulcer, guttural inflammation, conjunctival inflammation.

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indications of senility-related diseases, including periodontal inflammation, dental ulcer, guttural inflammation, conjunctival inflammation.

Results:

Senility is defined as the functional decline of various tissues and organs, including the changes in skin and appearance and the decline of physical strength and energy. What is more outstanding is the frequent attacks of various common diseases, including senility-related periodontal inflammation, dental ulcer, guttural inflammation and conjunctival inflammation. The HA fragment injections could rapidly treat senility-related periodontal inflammation, dental ulcer, guttural inflammation and conjunctival inflammation. The frequent attacks of periodontal inflammation, dental ulcer, guttural inflammation and conjunctival inflammation in old people were senility-related diseases and were associated with the current China's environment of air pollution, drinking water pollution and greater work stress. Among the 198 subjects, we analyzed 66 cases of periodontal inflammation, dental ulcer, guttural inflammation and conjunctival inflammation (36 cases in the experimental group 1 and 30 cases in the experimental group 2), and the results were as shown in Table 23:

TABLE 23

Therapeutic Effect of HA Fragment Injections on Periodontal Inflammation, Dental Ulcer, Guttural Inflammation and Conjunctival Inflammation.

|  | The inflammation and pain began to vanish within 1 day after 1 × 100 mg injection | Most of the inflammatory lesions were eliminated after 5 × 100 mg injections | The inflammatory lesions were almost eliminated after 6 × 100 mg injections | Number of samples |
|---|---|---|---|---|
| Periodontal Inflammation | 63 | 63 | 33 | 63 |
| Dental Ulcer | 4 | 8 | 4 | 8 |

TABLE 23-continued

Therapeutic Effect of HA Fragment Injections on Periodontal Inflammation, Dental Ulcer, Guttural Inflammation and Conjunctival Inflammation.

| | The inflammation and pain began to vanish within 1 day after 1 × 100 mg injection | Most of the inflammatory lesions were eliminated after 5 × 100 mg injections | The inflammatory lesions were almost eliminated after 6 × 100 mg injections | Number of samples |
|---|---|---|---|---|
| Inflammation of Pharynx and larynx | 53 | 53 | 53 | 53 |
| Conjunctival Inflammation | 36 | 66 | 66 | 66 |

Note:
Self-control was employed in this study, which refers to the comparison between the subject's current state (after treatment) the state of a period before treatment.

The results of Table 23 showed that the HA fragment injections had more rapid therapeutic effect on senility-related periodontal inflammation, dental ulcer, guttural inflammation and conjunctival inflammation than the previous local spray of HA fragment injection.

Conclusion: 1. The HA fragment injections via abdominal subcutaneous fat layer are used for effectively treating senility-related periodontal disease and dental ulcer, including the periodontal diseases and dental ulcer induced by chemotherapy and senility; 2. The HA fragment injections via abdominal subcutaneous fat layer are used for effectively treating senility-related guttural diseases, including the guttural diseases induced by chemotherapy and senility; 3. The HA fragment injections via abdominal subcutaneous fat layer are used for effectively treating senility-related conjunctival diseases, including the conjunctival diseases induced by chemotherapy and senility.

Embodiment 13

Objective: To further analyze the changes in the diseases and subclinical problems of the 198 subjects before and after treatment with HA fragment injections in "Embodiment 4", and to identify the new clinical indication of ankylosing spondylitis of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the I-HA fragment injections, so as to identify the therapeutic effect of the I-HA fragment injections on the new clinical indication of ankylosing spondylitis.

Results: HA fragment injections could effectively treat ankylosing spondylitis.

Ankylosing spondylitis is a disease of inflammatory pain and serious spinal deformation. Among the 198 subjects, we analyzed 3 cases of early ankylosing spondylitis (2 cases in the experimental group 1 and 1 case in the experimental group 2), and the results were as shown in Table 24:

TABLE 24

Therapeutic Effect of HA Fragment Injections on Ankylosing Spondylitis.

| | The pain began to relieve within 1 day after 1 × 100 mg injection | Most of the pain was eliminated after 5 × 100 mg injections | The pain was almost eliminated after 10 × 100 mg injections | Number of samples |
|---|---|---|---|---|
| Ankylosing Spondylitis | 3 | 3 | 3 | 3 |

Note:
Self-control was employed in this study, winch refers to the comparison between the subject's current state (after treatment) the state of a period before treatment.

Early ankylosing spondylitis was a disease of inflammatory pain. The analgesic effect of the HA fragment injection treatment showed that the inflammation of ankylosing spondylitis was reduced or eliminated, suggesting that the serious spinal deformation induced by inflammation would not develop continuously.

Conclusion: The I-HA fragment injections via abdominal subcutaneous fat layer are used for effectively treating painful early ankylosing spondylitis.

Embodiment 14

Objective: To further analyze the changes in the diseases and subclinical problems of the 198 subjects before and after treatment with HA fragment injections in "Embodiment 4", and to identify the new clinical indication of recovery of physical strength and energy after chemotherapy for tumor of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the I-HA fragment injections on the new clinical indication of recovery of physical strength and energy after chemotherapy for solid tumors.

Results:

HA fragment injection used for recovery of physical strength and energy after chemotherapy for tumor: Among the 198 subjects, we analyzed 32 cases requiring for the recovery of physical strength and energy after chemotherapy for tumor (17 cases in the experimental group 1 and 15 cases in the experimental group 2), and the results were as shown in Table 25:

TABLE 25

Therapeutic Effect of HA Fragment Injections on Recovery of Physical Strength and Energy and Alleviation of Chemotherapy-related Mucous Complications (Including the Symptoms and Signs of Oral, Guttural, Conjunctival and Intestinal Mucous Complications) After Chemotherapy for Solid Tumors.

|  | The physical strength and energy began to recover within 1 day after 1 × 100 mg injection | The physical strength and energy obviously recovered after 5 × 100 mg injections | The related mucous complications were obviously alleviated after 15 × 100 mg injections | Number of samples |
|---|---|---|---|---|
| After chemotherapy for pancreatic cancer | 7 | 7 | 7 | 7 |
| After operation and chemotherapy for gastric cancer | 5 | 5 | 5 | 5 |
| After radiotherapy and chemotherapy for lung cancer | 11 | 11 | 11 | 11 |
| After operation and chemotherapy for colorectal cancer | 1 | 1 | 1 | 1 |
| After chemotherapy for renal cancer | 3 | 3 | 3 | 3 |
| After operation and chemotherapy for ovarian cancer | 2 | 2 | 2 | 2 |
| After operation and chemotherapy for breast cancer | 3 | 3 | 3 | 3 |

Note:
Self-control was employed in this study, which refers to the comparison between the subject's current state (after treatment) the state of a period before treatment.

Conclusion: The HA fragment injections via abdominal subcutaneous fat layer are used for recovering physical strength and energy and effectively alleviating chemotherapy-related mucous complications after chemotherapy for different tumors.

Embodiment 15

Objective: To further analyze the changes in the diseases and subclinical problems of the 198 subjects before and after treatment with HA fragment injections in "Embodiment 4", and to identify the new clinical indication of lung cancer of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of lung cancer.

Results:

HA fragment injection used for treating late lung cancer: Among the 198 subjects, we analyzed 7 cases with late lung cancer underwent chemotherapy combined with HA fragment injection (5 cases in the experimental group 1 and 2 cases in the experimental group 2, once every 3~5 days for 12 consecutive months or till the death), and the results were as shown in Table 26:

TABLE 26

Therapeutic Effect of Chemotherapy Combined with HA Fragment Injections on Late Lung Cancer.

|  | Sizes of Lung cancer or the metastatic cancer of lung cancer was reduced | Lung cancer or the metastatic cancer of lung cancer did not keep growing and transfering | Survival >12 months for lung cancer after treatment | Number of samples |
|---|---|---|---|---|
| Chemotherapy Combined with HA Fragment Injection for Late Lung Cancer (Experimental Groups) | 4 | 7 | 6 | 7 |

TABLE 26-continued

Therapeutic Effect of Chemotherapy Combined with HA Fragment Injections on Late Lung Cancer.

| | Sizes of Lung cancer or the metastatic cancer of lung cancer was reduced | Lung cancer or the metastatic cancer of lung cancer did not keep growing and transfering | Survival >12 months for lung cancer after treatment | Number of samples |
|---|---|---|---|---|
| Chemotherapy for Late Lung Cancer (Control Group) | 2 | 0 | 1 | 7 |

Note:
Self-control was employed in the experimental group of this study, which refers to the comparison between the subject's current state (after treatment) the state of a period before treatment. The control group was other cases of late lung cancer under chemotherapy only.

In Table 26, a 64-year-old female subject was diagnosed with lung cancer of the right lung, accompanied by lymphatic metastasis of the left lung, brain, bone and mediastinum, which was inoperable for excision, and she was treated by radiotherapy and Tarceva chemotherapy. The subject was very weak after radiotherapy and chemotherapy, and started to receive 100 mg of HA fragment injection via abdominal subcutaneous fat layer, once every 3~5 days. The physical strength and energy of the subject began to recover on Day 1 of injection. After 3 months of injection, the CT examination showed that the tumor and metastatic mass were reduced. After 12 months of injection, she still lived normally at home and did not need hospitalization. The therapeutic results showed that the HA fragment injection could prevent the development and further metastasis of lung cancer and significantly prolong the survival.

In Table 26, a 78-year-old male subject was diagnosed with lung cancer of the right lung, accompanied by the lymphatic metastasis of mediastinum, which was inoperable for excision, and the molecular testing showed that the targeted drug chemotherapy would have no significant effect. The subject was still treated with chemical drugs, and started to receive 100 mg of HA fragment injection via abdominal subcutaneous fat layer, once every 3 days for a total of 3 months. The physical strength and energy of the subject began to recover on Day 3 of injection. After 3 months of injection, the CT examination showed that the tumor and metastatic mass were reduced. After 12 months of injection continuously, he still lived normally at home, the CT examination showed that the reduced tumor and metastatic mass did not develop further, and it was unnecessary to hospitalize for further treatment. The therapeutic results showed that the HA fragment injection could prevent the development and further metastasis of lung cancer.

HA fragment injections used for treating early lung cancer: Among the 198 subjects, we analyzed 5 cases of early lung cancer underwent operation combined with chemotherapy and HA fragment injection (3 cases in the experimental group 1 and 2 cases in the experimental group 2, once every 3~5 days for 3 consecutive months from 1 week preoperatively), and the results were as shown in Table 27:

TABLE 27

Effect of Operation Combined with Chemotherapy and HA Fragment Injections on Preventing Relapse of Early Lung Cancer.

| | The physical strength recovered to normal and maintained for >12 months after operation for lung cancer | Lung cancer did not relapse within 12 months | Survival >12 months for lung cancer after treatment | Number of samples |
|---|---|---|---|---|
| Operation Combined with B-HAHA fragment Injection for Early Lung Cancer (Experimental Groups) | 5 | 5 | 5 | 5 |
| Operation Combined with Chemotherapy for Early Lung Cancer (Control Groupantibiotics | 0 | 2 | 1 | 5 |

Note:
Self-control was employed in the experimental group of this study, which refers to the comparison between the subject's current state (after treatment) the state of a period before treatment. The control group was other cases treated by operation combined with chemotherapy only.

Conclusion: 1. The experimental results show that the HA fragment injections can prevent the development and further metastasis of late lung cancer; 2. The experimental results also show that the HA fragment injections could prevent the relapse of early lung cancer after operation.

Embodiment 16

Objective: To further analyze the changes in the diseases and subclinical problems of the 198 subjects before and after treatment with HA fragment injections in "Embodiment 4", and to identify the new clinical indication of pancreatic cancer of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the I-HA fragment injections, so as to identify the therapeutic effect of the I-HA fragment injections on the new clinical indication of pancreatic cancer.

Results:

Pancreatic cancer as a quite malignant tumor develops rapidly after metastasis, and it will lead to death within 90 days to the fastest. Foreign researches have shown that inflammation and tumor-related inflammatory cells may be the important stimulatives for the development and metastasis of pancreatic cancer.

HA fragment injections used for treating late pancreatic cancer: Among the 198 subjects, we analyzed 5 cases of late pancreatic cancer underwent operation combined with chemotherapy and HA fragment injections (3 cases in the experimental group 1 and 2 cases in the experimental group 2, once every 3~5 days for 12 consecutive months or till the death from 2 weeks preoperatively), and the results were as shown in Table 28:

TABLE 28

Therapeutic Effect of Chemotherapy Combined with B-HAHA Fragment Injections on Late Pancreatic Cancer.

| | Sizes of late pancreatic cancer or the metastatic mass of late pancreatic cancer was reduced | Late pancreatic cancer or the metastatic mass of late pancreatic cancer did not continue growing and transfering | Survival >12 months after treatment | Number of samples |
|---|---|---|---|---|
| Chemotherapy Combined with HA Fragment Injection for Late Pancreatic Cancer (Experimental Groups) | 2 | 4 | 4 | 5 |
| Chemotherapy for Late Pancreatic Cancer (Control Groupantibiotics | 0 | 0 | 0 | 5 |

Note:
Self-control was employed in the experimental group of this study, which refers to the comparison between the subject's current state (after treatment) the state of a period before treatment. The control group was other cases treated by chemotherapy.

In Table 28, a subject (male, 46 years old) after chemotherapy for pancreatic head cancer after chemotherapy was found that the pancreatic head cancer had transferred to liver due to jaundice, the bile duct was blocked to result in jaundice, the jaundice was solved by placing a stent through operation and nasobiliary drainage. He received chemotherapy monthly and was treated by traditional Chinese medicine at the same time. After 5×100 mg of HA fragment injections via abdominal subcutaneous fat layer, the physical strength and energy recovered; after 20×100 mg of HA fragment injections via abdominal subcutaneous fat layer, the ultrasonography showed that the pancreatic head cancer and the metastatic mass to liver began to reduce, and the subject worked normally for more than 90 days. The above results suggested that the HA fragment injection could promote the recovery of physical strength and energy after chemotherapy for solid tumors and might prevent the development and further metastasis of pancreatic head cancer by inhibiting inflammations. According to a foreign report (Halozyme Receives Orphan Drug Designation For PEGylated Recombinant Human Hyaluronidase PH20 For Pancreatic Cancer at: http://www.halozyme.com/Investors/News-Releases News-Release-Details/2014/Halozyme-Receives-Orphan-Drug-Designation-For-PEGylated-Recombinant-Human-Hyaluronidase-PH20~For-Pancreatic-Cancer/default.aspx#sthash.aLjvxToQ.dpuf), long-acting hyaluronidase PEGPH20 combined with chemotherapy effectively prolongs the survival of patients with pancreatic cancer, and the experimental results indicate that the mechanism of action might be that the LMW-HA fragment injection similar to the invention is produced using HA in human body.

Conclusion: The experimental results show that the HA fragment injections can prevent the development and further metastasis of late pancreatic cancer and obviously prolong the survival.

Embodiment 17

Objective: To further analyze the changes in the diseases and subclinical problems of the 198 subjects before and after treatment with HA fragment injections in "Embodiment 4", and to identify the new clinical indication of gastric cancer of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of gastric cancer.

Results:

HA fragment injections used for treating late gastric cancer: Among the 198 subjects, we analyzed 4 cases of late gastric cancer underwent operation combined with chemotherapy and HA fragment injections (3 cases in the experimental group 1 and 1 case in the experimental group 2, once every 1~5 days for >12 consecutive months), and the results were as shown in Table 29:

TABLE 29

Therapeutic Effect of Chemotherapy Combined with B-HAHA Fragment Injections on Late Gastric Cancer.

| | Sizes of late gastric cancer or the metastatic mass of late gastric cancer was reduced | Late gastric cancer or the metastatic mass of late gastric cancer did not continue growing and transfering | Survival >12 months after treatment | Number of samples |
|---|---|---|---|---|
| Chemotherapy Combined with HA Fragment Injection for Late Gastric Cancer (Experimental Groups) | 2 | 5 | 5 | 5 |
| Chemotherapy for Late Gastric Cancer (Control Groupantibiotics | 0 | 2 | 2 | 5 |

Note:
Self-control was employed in the experimental group of this study, which refers to the comparison between the subject's current state (after treatment) the state of a period before treatment. The control group was other cases treated by chemotherapy.

In Table 29, a subject (male, 62 years old) after chemotherapy for gastric cancer had multiple metastasis of gastric cancer, and the metastatic mass in brain compressed the respiratory center to cause dyspnea, and he was rescued in the ICU. He was treated by 100 mg of HA fragment injection via abdominal subcutaneous fat layer, once a day for 20 consecutive days. At Day 10 after HA fragment injection, the subject breathed smoothly with the physical strength and energy recovered, and he was discharged to go home for rehabilitation. After discharge, the subject was injected with 100 mg of HA fragment injection via abdominal subcutaneous fat layer at home, once every 3~5 days for 12 consecutive months or more.

Conclusion: The experimental results show that the HA fragment injections can prevent the development and further metastasis of late gastric cancer and obviously prolong the survival.

Embodiment 18

Objective: To further analyze the changes in the diseases and subclinical problems of the 198 subjects before and after treatment with HA fragment injections in "Embodiment 4", and to identify the new clinical indication of ovarian cancer of the HA fragment injections (I-A fragment injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of ovarian cancer.

Results: HA fragment injection used for treating late ovarian cancer: Among the 198 subjects, we analyzed 5 cases of late ovarian cancer underwent chemotherapy combined with HA fragment injection (2 cases in the experimental group 1 and 3 case in the experimental group 2, once every 3 days for 3 consecutive months), and the results were as shown in Table 30:

TABLE 30

Therapeutic Effect of Chemotherapy Combined with B-HAHA Fragment Injections on Late Ovarian Cancer.

| | Late ovarian cancer or the metastatic mass of late ovarian cancer did not continue growing and transfering | CA125 was slightly lowered after treatment | CA125 was significantly lowered after treatment | Number of samples |
|---|---|---|---|---|
| Chemotherapy Combined with HA Fragment Injection for Late Ovarian Cancer (Experimental Groups) | 5 | 0 | 5 | 5 |

TABLE 30-continued

Therapeutic Effect of Chemotherapy Combined with B-HAHA Fragment Injections on Late Ovarian Cancer.

| | Late ovarian cancer or the metastatic mass of late ovarian cancer did not continue growing and transfering | CA125 was slightly lowered after treatment | CA125 was significantly lowered after treatment | Number of samples |
|---|---|---|---|---|
| Chemotherapy for Late Ovarian Cancer (Control Group) | 1 | 3 | 1 | 5 |

Note:
Self-control was employed in the experimental group of this study, which refers to the comparison between the subject's current state (after treatment) the state of a period before treatment. The control group was other cases treated by chemotherapy.

In Table 30, a subject (female, 62 years old) after operation and chemotherapy for ovarian cancer was extremely weak due to the chemotherapy and radiotherapy for lymphatic metastasis, and she had to stay in bed all day. She was injected with 20×100 mg of HA fragment injections via abdominal subcutaneous fat layer, the physical strength and energy began to recover on Day 2 after 1×100 mg; at the end of 20×100 mg injections, CA125 was surprisingly reduced to 50 U/ml from 500 U/ml before treatment, and the tumor and metastatic mass were reduced, indicating that the HA fragment injection could promote the recovery of physical strength and energy after chemotherapy for treating ovarian cancer and might prevent the development and further metastasis of ovarian cancer by inhibiting inflammations.

Conclusion: The experimental results show that the HA fragment injections can lower CA125 as a cancer indicator for late ovarian cancer and control the continuous growth and metastasis of late ovarian cancer or the metastatic mass of late ovarian cancer.

Embodiment 19

Objective: To further analyze the changes in the diseases and subclinical problems of the 198 subjects before and after treatment with HA fragment injections in "Embodiment 4", and to identify the new clinical indication of oral cancer with difficulty in eating of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HI-A fragment injections, so as to identify the therapeutic effect of the HA fragment injections on the new clinical indication of oral cancer with difficulty in eating.

Results: HA fragment injections used for treating oral cancer: Among the 198 subjects, we analyzed 10 cases of oral cancer with obvious difficulty in eating treated by HA fragment injection (6 cases in the experimental group 1 and 4 cases in the experimental group 2, once a day for 15 injections consecutively for those in the experimental group in the Table, and injection of normal saline+oral administration of antibiotics metronidazole for those in the control group), and the results were as shown in Table 31:

TABLE 31

Therapeutic Effect of HA Fragment Injections on Oral Cancer with Obvious Difficulty in Eating

| | The mass of oral cancer and the induced inflammation became smaller and vanished | The mass of oral cancer did not become smaller and vanished | The difficulty in eating induced by the mass of oral cancer almost disappeared | Number of samples |
|---|---|---|---|---|
| HA Fragment Injection + Oral Administration of Antibiotics Metronidazole (Experimental Groups) | 5 | 0 | 5 | 5 |
| Injection of normal saline + Oral Administration of Antibiotics Metronidazole (Control Groupantibiotics | 2 | 3 | 1 | 5 |

Conclusion: The experimental results show that the HA fragment injections can be used for treating oral cancer with obvious difficulty in eating.

Embodiment 20

Objective: To further analyze the changes in the diseases and subclinical problems of the 198 subjects before and after treatment with HA fragment injections in "Embodiment 4", and to identify the new clinical indication of postoperative relapse of meningioma of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of postoperative relapse of meningioma.

Figure 11:
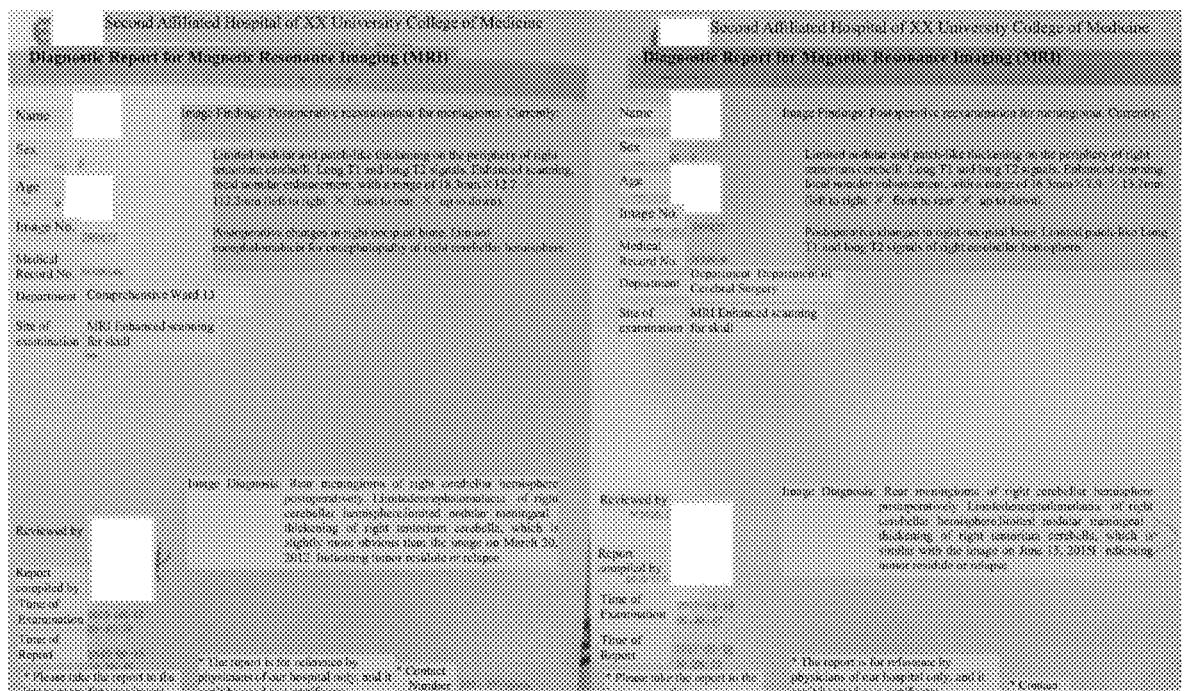
FIG. 11 shows the enhanced MRI reports before and after the treatment with injection of LMW-HA fragments for a case of meningioma.

Results:

HA fragment injection used for treating postoperative relapse of meningioma: Among the 198 subjects, we analyzed 5 cases of postoperative relapse of meningioma treated by HA fragment injection (3 cases in the experimental group 1 and 2 cases in the experimental group 2, once every 3~5 day for 12 consecutive months), and the results were as shown in Table 32:

times within the following 12 months. The results of enhanced MRI showed that the focus of previous meningioma residule or relapse was reduced from 8.3×12.7×112.2 mm to 16.3×7.9×13.2 mm (FIG. 11), the focus was reduced instead of growing continuously, and finally the subject did not suffer from the attack of headache any more. The above results showed that the HA fragment injection could be used for treating meningioma or the postoperative relapse of meningioma.

Conclusion: The experimental results show that the HI-A fragment injections can control the postoperative relapse of meningioma.

Embodiment 21

Objective: To further analyze the changes in the diseases and subclinical problems of the 198 subjects before and after treatment with HA fragment injections in "Embodiment 4", and to identify the new clinical indication of functional recovery after cerebral embolism of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA

TABLE 32

Therapeutic Effect of HA Fragment Injections on Postoperative Relapse of Meningioma.

|  | The headache symptom and number of attacks were obviously relieved or disappeared | The headache symptom and number of headaches were aggravated or increased | The enhanced MRI showed that the meningioma residule did not continue to thicken or relapse | Number of samples |
|---|---|---|---|---|
| HA Fragment Injection Experimental Groups | 5 | 0 | 5 | 5 |
| Blank Control Group | 0 | 5 | 0 | 5 |

Note:
Self-control was employed in the experimental group of this study, which refers to the comparison between the subject's current state (after treatment) the state of a period before treatment. The control group was other cases given blank treatment.

In Table 32, a female subject (62 years old) was diagnosed with meningioma by enhanced MRI for frequent headache in 2007, and the headache disappeared after operation in the same year. From 2015, the headache attacked frequently, and she was diagnosed with meningioma residule or relapse by enhanced MRT, namely that the meninges was obviously thickened. After 100 mg of HA fragment injection via abdominal subcutaneous fat layer for 15 times, the attacks of headache were obviously reduced. The subject continued the injection once every 5 days, 100 mg every time for about 60 fragment injections on the new clinical indication of functional recovery after cerebral embolism.

Result 1: HA fragment injection used for functional recovery after cerebral embolism: Among the 198 subjects, we analyzed 3 cases requiring for functional recovery for the stiffness of upper limbs after cerebral embolism (3 cases in the experimental group 1, 1 injection every 2 days for 10 times consecutively), and the results were as shown in Table 33:

TABLE 33

Effect of HA Fragment Injections on Functional Recovery
for the Stiffness of Upper Limbs After Cerebral Embolism

|  | The stiffness of upper limbs and the failure in relaxing fingers began to turn better within 1 day after 1 × 100 mg injection | The stiffness of upper limbs and the failure in relaxing fingers obviously turned better after 5 × 100 mg injections | The stiffness of upper limbs and the failure in relaxing fingers further turned better after 10 × 100 mg injections | Number of samples |
|---|---|---|---|---|
| HA Fragment Injection | 3 | 3 | 3 | 3 |

Note:
Self-control was employed in this study, which refers to the comparison between the subject's current state (after treatment) the state of a period before treatment.

In Table 33, 1 male subject (79 years old) had suffered from cerebral embolism for 3 years, and he had the feel of cold on the whole body, stiffness of upper limbs and failure in relaxing fingers. After 10×100 mg HA fragment injections via abdominal subcutaneous fat layer, the symptoms and signs of feel of cold on the whole body, stiffness of upper limbs and failure in relaxing fingers obviously turned better, and he required to receive the HA fragment injection continuously.

In Table 33, 1 male subject (56 years old) had suffered from cerebral embolism for 1 year, and he had the stiffness of upper limbs, failure in relaxing fingers and numbness in fingers. After 10×100 mg HA fragment injections via abdominal subcutaneous fat layer, the symptoms and signs of stiffness of upper limbs, failure in relaxing fingers and numbness in fingers obviously turned better.

In Table 33, 1 male subject (82 years old) had suffered from cerebral embolism for 8 years, and he had the stiffness of upper limbs, failure in relaxing fingers and pain in fingers. After 10×100 mg HA fragment injections via abdominal subcutaneous fat layer, the symptoms and signs of stiffness of upper limbs and failure in relaxing fingers obviously turned better.

V. Result 2: HA fragment injections used for functional recovery after cerebral embolism: Among the 198 subjects, we analyzed 4 cases requiring for functional recovery for the weakness of upper limbs after cerebral embolism (1 case in the experimental group 1 and 3 cases in the experimental group 2), and the results were as shown in Table 34:

TABLE 34

Effect of HA Fragment Injections on Functional Recovery After Cerebral Embolism

|  | The energy and physical strength were improved within 1 day after 1 × 100 mg injection | The weakness in half body slightly turned better and it was a little stronger to walk or the vision began to turn better after 5 × 100 mg injections | The weakness in half body obviously turned better and it was strong to walk or the vision obviously turned better after 10 × 100 mg injections | Number of samples |
|---|---|---|---|---|
| Weakness in Half Body, Feebleness in Walking | 3 | 3 | 3 | 3 |
| Diminution of Vision | 1 | 1 | 1 | 1 |

Note:
Self-control was employed in this study, which refers to the comparison between the subject's current state (after treatment) the state of a period before treatment.

In Table 34, 1 male subject (67 years old) had suffered from cerebral embolism for 30 days, and he was weak in half body and feeble in walking. After 10×100 mg HA fragment injections via abdominal subcutaneous fat layer, the weakness in half body obviously turned better, and he was strong to walk, indicating that the HA fragment injection could be used for the functional recovery after cerebral embolism.

In Table 34, 1 male subject (59 years old) had suffered from cerebral embolism for 4 days, and he could only see the objects within 20 cm due to the impaired vision. After 10×100 mg HA fragment injections via abdominal subcutaneous fat layer, the vision obviously turned better, and he could see the objects within 40 cm, indicating that the HA fragment injection could be used for the functional recovery after cerebral embolism.

Conclusion: The HA fragment injections via abdominal subcutaneous fat layer can effectively promote the functional recovery after cerebral embolism.

Embodiment 22

Objective: To further analyze the changes in the diseases and subclinical problems of the 198 subjects before and after treatment with HA fragment injections in "Embodiment 4", and to identify the new clinical indication of angina of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of angina.

HA fragment injections used for treating angina induced by cardiovascular diseases: Coronary heart disease, complications after intravascular stent and other cardiovascular diseases are essentially chronic inflammatory diseases, and the effective methods for prevention and treatment are in urgent need. Among the 198 subjects treated by HA fragment injections, we analyzed 6 cases of angina (3 cases in the experimental group 1 and 3 cases in the experimental group 2, once a day for 20 injections consecutively), and the results were as shown in Table 35:

Conclusion: The results of Table 35 show that the HA fragment injection via abdominal subcutaneous fat layer can effectively treat the angina induced by cardiovascular diseases.

Embodiment 23

Objective: To further analyze the changes in the diseases and subclinical problems of the 198 subjects before and after treatment with HA fragment injections in "Embodiment 4", and to identify the new clinical indication of painful gout during attack of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indications of painful gout during attack.

HA fragment injections used for treating gout: Among the 198 subjects treated by HA fragment injections, we analyzed 5 cases of painful gout during attack (3 cases in the experimental group 1 and 2 cases in the experimental group 2, once a day for 5 times consecutively), and the results were as shown in Table 36:

TABLE 35

Therapeutic Effect of HA Fragment Injections on Angina Induced by Cardiovascular Diseases.

| | The energy and physical strength were improved within 1 day after 1 injection | The attacks of angina were obviously reduced after 10 injections | Angina did not relapse within 60 days after 20 injections | Number of samples |
|---|---|---|---|---|
| Coronary Heart Diseases | 3 | 3 | 3 | 3 |
| Complications after intravascular stent | 3 | 3 | 3 | 3 |

Note:
Self-control was employed in this study, which refers to the comparison between the subject's current state (after treatment) the state of a period before treatment.

TABLE 36

Therapeutic Effect of HA Fragment Injections on Painful Gout During Attack.

| | The symptom of pain was obviously relieved after 1 injection | The sign of red and swelling toes was obviously relieved after 1 injection | The symptom of pain and the sign of red and swelling toes almost disappeared after 5 injections | Number of samples |
|---|---|---|---|---|
| HA Fragment Injection | 5 | 5 | 5 | 5 |

Note:
Self-control was employed in this study, which refers to the comparison between the subject's current state (after treatment) the state of a period before treatment.

Conclusion: The results of Table 36 showed that the HA fragment injection via abdominal subcutaneous fat layer can effectively treat painful gout during attack.

Embodiment 24

Objective: To further analyze the changes in the diseases and subclinical problems of the 198 subjects before and after treatment with HA fragment injections in "Embodiment 4", and to identify the new clinical indication of arthritis never treated by cortical hormone of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of arthritis never treated by cortical hormone.

HA fragment injections used for treating arthritis never treated by cortical hormone: Among the 198 subjects treated by HA fragment injections, we analyzed 6 cases of arthritis never treated by cortical hormone (3 cases in the experimental group 1 and 2 cases in the experimental group 2, once a day for 15 times consecutively), and the results were as shown in Table 37:

TABLE 37

Therapeutic Effect of HA Fragment Injections on Arthritis Never Treated by Cortical Hormone.

| | The symptom of arthralgia began to relieve after 1 injection | The sign of redness and swelling of joint began to relieve after 1 injection | The symptom of arthralgia and the sign of redness and swelling of joint were obviously relieved after 15 injections | Number of samples |
|---|---|---|---|---|
| Osteoarthritis | 3 | 0 | 3 | 3 |
| Rheumatic Arthritis | 2 | 0 | 3 | 3 |

Note:
Self-control was employed in this study, which refers to the comparison between the subject's current state (after treatment) the state of a period before treatment.

HA fragment injections used for treating arthritis previously treated by cortical hormone: Among the 198 subjects treated by HA fragment injections, we analyzed 4 cases of arthritis previously treated by cortical hormone (2 cases in the experimental group 1 and 2 cases in the experimental group 2, once a day for 15 times consecutively), and the results were as shown in Table 38:

TABLE 38

Therapeutic Effect of HA Fragment Injection on Arthritis Previously Treated by Cortical Hormone.

|  | Compared with that before treatment, the symptom of arthralgia began to relieve after 1 injection | Compared with that before treatment, the sign of redness and swelling of joint began to relieve after 1 injection | Compared with those before treatment, the symptom of arthralgia and the sign of redness and swelling of joint were obviously relieved after 15 injections | Number of samples |
|---|---|---|---|---|
| Osteo-arthritis | 0 | 0 | 1 | 2 |
| Rheumatic Arthritis | 0 | 0 | 0 | 2 |

Note:
Self-control was employed in this study, which refers to the comparison between the subject's current state (after treatment) the state of a period before treatment.

Conclusion: 1. The HA fragment injection via abdominal subcutaneous fat layer can effectively treat arthritis never treated by cortical hormone; 2. The HA fragment injection via abdominal subcutaneous fat layer had no therapeutic effect on arthritis previously treated by cortical hormone.

Embodiment 25

Objective: To further analyze the changes in the diseases and subclinical problems of the 198 subjects before and after treatment with HA fragment injections in "Embodiment 4", and to identify the new clinical indication of herpes zoster with serious pain of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of herpes zoster with serious pain.

HA fragment injections used for treating herpes zoster with serious pain: Among the 198 subjects treated by HA fragment injections, we analyzed 5 cases of herpes zoster with serious pain (2 cases in the experimental group 1 and 2 cases in the experimental group 3, once a day for 10 times consecutively), and the results were as shown in Table 39:

TABLE 39

Therapeutic Effect of HA Fragment Injections on Herpes Zoster with Serious Pain.

|  | The symptom of pain was obviously relieved after 1 injection | The symptom of pain almost disappeared after 10 injections | Number of samples |
|---|---|---|---|
| HA Fragment Injection | 5 | 5 | 5 |

Note:
1. Self-control was employed in this study, which refers to the comparison between the subject's current state (after treatment) the state of a period before treatment;
2. In the untreated blank control group, the pain was aggravated in 2 cases and the pain was not relieved in 3 cases within 10 days.

Conclusion: The results of Table 39 show that the HA fragment injections via abdominal subcutaneous fat layer can effectively treat herpes zoster with serious pain.

Embodiment 26

Objective: To further analyze the changes in the diseases and subclinical problems of the 198 subjects before and after treatment with HA fragment injections in "Embodiment 4", and to identify the new clinical indication of acute pancreatitis with serious pain of the HA fragment injections (HA fragment Injections 1 and 2 in Embodiment 1).

Methods: The changes in the diseases and subclinical problems of the 198 subjects before and after treatment with HA fragment injections in "Embodiment 4" were further analyzed, including medical history, symptoms, signs and laboratory results before injection, and the changes in symptoms, signs and laboratory results after the HA fragment injections, so as to identify the therapeutic effect of the HA fragment injections on the new clinical indication of acute pancreatitis with serious pain.

HA fragment injections used for acute pancreatitis with serious pain: Among the 198 subjects treated by HA fragment injections, we analyzed 6 cases of acute pancreatitis with serious pain (3 cases in the experimental group 1 and 3 cases in the experimental group 2, in the table below the experimental groups were injected with HA fragment injection+antibiotics for once a day, and the control group was injected with antibiotics for once a day, for 10 injections consecutively), and the results were as shown in Table 40:

TABLE 40

Therapeutic Effect of HA Fragment Injections on Acute Pancreatitis.

| | The symptom of pain started to relieve on after 1 day of injection | The symptom of pain was obviously relieved and the subject ate liquid food after 3 days of injection | The symptom of pain disappeared and the subject ate normal food after 10 days of injection | Number of samples |
|---|---|---|---|---|
| HA Fragment Injection + Antibiotics (Experimental Groups) | 3 | 3 | 3 | 3 |
| Antibiotics (Control Group) | 0 | 0 | 0 | 3 |

Note:
Self-control was employed in the experimental group of this study, which refers to the comparison between the subject's current state (after treatment) the state of a period before treatment.

Conclusion: The results of Table 40 show that the HA fragment injection via abdominal subcutaneous fat layer can effectively treat acute pancreatitis with serious pain.

Embodiment 27

Objective: To compare the studies on subcutaneous injection of LMW-HA fragments produced by different methods on dogs and human subjects.

Methods: In Embodiment 1 of the invention, the HMW-HA raw material was directly digested using human recombinant hyaluronidase to produce HA fragment Injection 1 and Injection 2 (with a molecular weight distribution of 10~60 KD), and the injection deep into abdominal subcutaneous fat layer did not cause pain in the above embodiment.

In the previous research achievement (Application No.: 201410153593.5, Publication No.: CN105018547A) of the applicant, it is also recorded that HMW-HA raw material was firstly baked and heated to reduce the molecular weight of HMW-HA raw material, and then HMW-HA was digested by recombinant human hyaluronidase to produce the LMW-HA fragments.

In this embodiment, the step of baking HMW-HA raw material is added in reference to the above method. The baking aims to reduce the molecular weight of HMW-HA raw material and reduce the viscosity after dissolution using the physical method. Besides, owing to the reduction in the molecular weight of HMW-HA raw material after baking, the amount of recombinant human hyaluronidase used for subsequent digestion can be further reduced to greatly lower the cost.

In implementation, except the baking step, the rest of steps are the same as those in Embodiment 1. Specifically, the process of implementation can follow the specific steps below:

Use an enzyme digestion and blending tank with a working volume of 25 L for cleaning and sterilization in-place, and prepare injection-grade HA raw material with a molecular weight distribution of 800~1,200 KD (the same as those in Embodiment 1);

Treat the injection-grade HA raw material with a molecular weight distribution of 800~1,200 KD as below: Bake at 120° C. for 1~2 h (treatment 1) or bake at 105° C. for 5~6 h (treatment 2);

Add injection-grade pure water into the injection-grade HA raw material with a molecular weight distribution of 800~1,200 KD after baking by one time or several times, then add 80~90 mM of sodium chloride, 1 mM of magnesium ions and 4,000~5,000 units of recombinant human hyaluronidase (the preparing method is the same as that in Embodiment 1) per 1 g of HMW-HA raw material in order, mix them completely, and react at 37° C. for 5~6 h until that the molecular weight of HA fragments reaches 10 KD-60 KD. Add 35~45 mM of sodium chloride to regulate the osmotic pressure to 280~300 mOsm/L, then heat it at 84~95° C. for 30~60 min (thermal inactivation of recombinant human hyaluronidase, partial bacteria inactivation and virus inactivation for reducing the pH), and then filter bacteria at 0.22 μm.

The HA fragment injection was prepared after filtration, comprising:

Injection 3 (by treatment 1, including the step of baking at 120° C.):

Each 2~4 ml contained 100 mg of HA fragments with a molecular weight distribution of 10 KD~60 KD and <20 μg of protein residue of inactivated recombinant human hyaluronidase PH20 without enzyme activity (endotoxin <0.5 IU/ml, sterile, virus-free), the final concentration of sodium chloride was 115~125 mM, and the final concentration of magnesium ions was 1 mM.

Injection 4 (by treatment 2, including the step of baking at 105° C.):

Each 2~4 ml contained 100 mg of HA fragments with a molecular weight distribution of 10 KD~60 KD and <20 μg of protein residue of inactivated recombinant human hyaluronidase PH20 (endotoxin <0.5 IU/ml, sterile, virus-free), the final concentration of sodium chloride was 115~125 mM, and the final concentration of magnesium ions was 1 mM.

The LMW-HA fragment Injection 3 and Injection 4 as well as Injection 1 in the above embodiment produced by different methods were used for subcutaneous injection on dogs and human, and it was found that Injection 3 induced the side effect of pain in injection. The pain in dogs was demonstrated by the fierce flounder at the beginning of injection and in the process of injection, and the pain in subjects was demonstrated by complaining about the pain to the injector and requiring stopping the injection immediately.

Results: See Table 41.

TABLE 41

Results of Study on Subcutaneous Injection of LMW-HA Fragments Produced by Different Methods in Causing Pain for Dogs and Human.

| Production Method of LMW-HA Fragment Injection | Number of Samples | Manner of Injection | Dog | Subject |
| --- | --- | --- | --- | --- |
| Baking at 120° C. for 1~2 h + Subsequent Enzyme Digestion by Recombinant Human Hyaluronidase (Injection 3) | 3 | Subcutaneous | The dog floundered fiercely at the beginning of injection and in the process of injection | The subject felt painful as soon as the injection began and required stopping the injection immediately |
| Baking at 105° C. for 5~6 h + Subsequent Enzyme Digestion by Recombinant Human Hyaluronidase (Injection 4) | 3 | Subcutaneous | The dog was quiet at the beginning of injection and in the process of injection | The subject did not feel painful and kept quiet at the beginning of injection and in the process of injection |
| Direct Enzyme Digestion by Recombinant Human Hyaluronidase Without Baking in Advance (Injection 1) | 3 | Subcutaneous | The dog was quiet at the beginning of injection and in the process of injection | The subject did not feel painful and kept quiet at the beginning of injection and in the process of injection |

Conclusion: 1. Unexpectedly, the subcutaneous injection of LMW-HA fragments produced by baking at 120° C. causes serious pain for dogs and subjects, and it can't be used for injection; 2. Unexpectedly, the subcutaneous injection of LMW-HA fragments produced by baking at 105° C. does not cause pain for dogs and subjects, and it can be used for injection (the injection also has a therapeutic effect on the above diseases or symptoms in subjects only with enough sample number in order to achieve statistical significance, and the specific results are not listed here. Besides, in consideration to the production cost, the HA fragment injection produced by this production method is applicable for developing into products for experimental animals or for veterinary use.); 3. The subcutaneous injection of LMW-HA fragments produced without baking and directly by enzyme digestion using recombinant human hyaluronidase does not cause pain for dogs and subjects, and it can be used for injection.

Embodiment 28

Objective: To explore the possibility for activation and commercialized production of LMW-HA fragments with the therapeutic effect in the above embodiments by the digestion using other types of hyaluronidase.

Methods: (1) Study the production methods of multiple hyaluronidases and the results of producing LMW-HA fragments by enzyme digestion of HMW-HA found in the existing references; (2) Produce different hyaluronidases independently or cooperatively, and verify the feasibility in enzyme digestion and activation of HMW-HA; (3) Study what kind of hyaluronidase can digest and activate HMW-HA to the corresponding molecular weight? Which kind of end structure of enzyme digestion can activate LMW-HA to have the therapeutic effect of the HA fragment injections shown in the above embodiments? Which kind of hyaluronidase residule will not cause allergic reaction in human?

Results and Discussions: By combining with the production methods of multiple hyaluronidases and the methods for enzyme digestion of HMW-HA, the research results are respectively reported as below:

1. In addition to neutral human acrosome hyaluronidase PH20 (or Hyal3 or SPAM1) in this study, human also has hyaluronidase 1-Hyal1 and Hyal2 in cells. According to the reference "Recombinant human hyaluronidase Hyal-1: Insect cells versus *Escherichia coli* as expression system and identification of low molecular weight inhibitors, Glycobiology, 17(4):444-53, 2007", it has been found that recombinant human Hyal1 hyaluronidase produced by insect cell *Drosophila* Schneider-2 (DS-2) has the specific activity of 8.6 U/mg and the best reaction pH value of 3.5~4.0, but such production method has a very low output, and it is not applicable for activation and commercialized production of LMW-HA fragment injection. In addition, we produce recombinant human Hyal1 and Hyal2 proteins using zooblast (CHO-S cells), pMH3, pMH4 and pMH5 expression vectors rich in GC, and human Hyal1 and Hyal2 cDNA by the construction manner of the expression system in Embodiment 1. It is found that the activities of the obtained hyaluronidases Hyal1 and Hyal2 are significantly lower than PH20 (1×105 U/mg zymoprotein) produced at present, indicating that the recombinant human Hyal1 and Hyal2 are not applicable for producing zooblasts.

2. The output of yeast-expressed neutral human acrosome hyaluronidase PH20 (or Hyal3 or SPAM1) can reach the level of commercialization, with the specific activity up to 10,000 IU/mg zymoprotein, and it is applicable for digestion, activation and commercialized production of LMW-HA fragment injection. We use the yeast-expressed neutral human acrosome hyaluronidase PH20, after enzyme digestion, affinity column chromatography, precipitation, column chromatography, dialysis, ultrafiltration concentration, etc. are used in order or respectively for recombinant human hyaluronidase to remove the contained protein residue of recombinant human hyaluronidase and produce the HA fragment injection similar to HA fragment Injection 2 in Embodiment 1 (HA fragments with a molecular weight distribution of 10 KD-60 KD 100 mg/2~4 ml, 115~125 mM of sodium chloride and 1 mM of magnesium ions) not containing protein residue of recombinant human hyaluronidase, and a clinical study was carried out for 38 subjects of multiple senility-related diseases. According to the results of Table 42, although yeast-expressed neutral human acrosome hyaluronidase PH20 had a lower specific activity, it had certain influence on the purity of HA fragment injection, and it could be used for producing HA fragment injection having a therapeutic effect on human and without allergic side effect by removing the contained protein residue of recombinant human hyaluronidase.

TABLE 42

Clinical Effect of HA Fragment Injection 2 Produced by Using Yeast-expressed Neutral Human Acrosome Hyaluronidase PH20 in 38 Subjects of Multiple Senility-related Diseases

| Indication | Number of samples with effective treatment | Number of researched samples |
| --- | --- | --- |
| Facial cosmetology and facial anti-aging | 38 | 38 |
| Pain relief | 12 | 12 |
| Itching relief | 7 | 7 |
| Enhancing physical strength and energy | 36 | 38 |
| Reducing subcutaneous fat in head, face and neck | 36 | 38 |
| Myofascitis | 7 | 7 |
| Cervical Spondylosis | 4 | 4 |
| Itching Senile Eczema | 3 | 3 |
| Recovering Physical Strength and preventing the metastasis of solid tumors after chemotherapy for solid tumors | 1 | 1 |
| Functional recovery after cerebral infarction | 2 | 2 |
| Periodontal inflammation | 18 | 18 |
| Dental ulcer | 4 | 4 |
| Guttural inflammation | 14 | 14 |
| Conjunctival inflammation | 5 | 5 |

Note:
Self-control was employed in this study, which refers to the comparison between the subject's current state (after treatment) the state of a period before treatment.

3. We produce the fusion protein of neutral human acrosome hyaluronidase PH20 from the oily seed expression system using the plant of *Arabidopsis thaliana* through a partner laboratory, and it is found that it can be used for producing the above HA fragment injection having a therapeutic effect on human and without allergic effect, see Table 43 for the specific effects. Compared with the high-purity glycosylated recombinant human hyaluronidase produced from the zooblast of Chinese hamster ovary cells, this method for producing the fusion protein of hyaluronidase PH20 has low cost, high output and low activity, but the cost is slightly higher for removing the contained fusion protein of hyaluronidase PH-20. In addition, based on our previous research achievements in LMW-HA for external use, we believe that the plant expressed hyaluronidase PH20 is applicable for producing LMW-HA aerosol, spray, gel preparations, etc. for external use requiring for low purity.

TABLE 43

Clinical Effect of HA Fragment Injection 2 Produced by Using Plant-expressed Neutral Human Acrosome Hyaluronidase PH20 in 35 Subjects of Multiple Senility-related Diseases

| Indication | Number of samples with effective treatment | Number of researched samples |
| --- | --- | --- |
| Facial cosmetology and facial anti-aging | 35 | 35 |
| Pain relief | 15 | 15 |
| Itching relief | 7 | 7 |
| Enhancing physical strength and energy | 30 | 35 |
| Reducing subcutaneous fat in head, face and neck myofascitis | 30 | 35 |
| | 7 | 7 |
| Myofascitis | 4 | 4 |
| Cervical Spondylosis | 3 | 3 |
| Itching Senile Eczema | 1 | 1 |
| Recovering Physical Strength and preventing the metastasis of solid tumors after chemotherapy for solid tumors | 2 | 2 |
| Periodontal inflammation | 16 | 16 |
| Dental ulcer | 4 | 4 |
| Guttural inflammation | 13 | 13 |
| Conjunctival inflammation | 5 | 5 |

Note:
Self-control was employed in this study, which refers to the comparison between the subject's current state (after treatment) the state of a period before treatment.

4. The hyaluronidase extracted from goat or bovine testes is mainly neutral goat or bovine acrosome hyaluronidase PH20, and the skin allergy test is required before use for human. Though such hyaluronidase has low cost, it also has low purity, and the cost is also high for removing the protein residules of hyaluronidase. Compared with high-purity glycosylated recombinant human hyaluronidase produced from the zooblast of Chinese hamster ovary cells, it is believed that it is not applicable for producing the HA fragment injection having a therapeutic effect on human, without allergic side effect and requiring for high purity.
5. According to the Patent WO/2014/165713 of CEDARS-SINAI MEDICAL CENTER, LMW-HA less than 10 KD generated by streptococci hyaluronidase does not cause inflammatory reactions, but LMW-HA greater than 10 KD generated by *Streptomyces* hyaluronidase causes inflammatory reactions, and these are contradictive to our HA fragment with a molecular weight distribution of 10 KD-60 KD having a therapeutic effect; however, it shall be mainly considered here that the protein residue of bacterial hyaluronidase may induce allergic reactions for human, and it is not applicable for producing the HA fragment injection having a therapeutic effect on human, without allergic side effect and requiring for high purity.
6. Hyaluronidase bee venom has strong allergen property, and it can cause allergic reaction for human in addition to promoting the absorption of bee venom. The hyaluronidase extracted from bee venom and the microorganism-expressed hyaluronidase in bee venom are both not applicable for producing the HA fragment injection having a therapeutic effect on human, without allergic side effect and requiring for high purity.
7. Leech hyaluronidase secreted by hematophagous leech can dissolve skin and help the leech enter human body to suck blood. According to the references of "Enzymatic production of specifically distributed hyaluronan oligosaccharides, Carbohydr Polym, 2015, 129:194-200" and "High-yield novel leech hyaluronidase to expedite the preparation of specific hyaluronan oligomers (2014), Scientific Reports 4, Article number 4471", the yield, digestion activity and cust of the fusion protein of leech hyaluronidase in yeast expression can meet the requirement for commercialization and can digest HMW-HA into LMW-HA. However, the residue of leech hyaluronidase can cause allergic reactions, and it can be used for producing the HA fragment injection having a therapeutic effect on human shown in the above embodiments, without allergic side effect and requiring for high purity only by complete elimination.

Therefore, by summarizing the above research results, we believe that in the process of producing LMW-HA fragments in the invention, the applicable recombinant human hyaluronidase can be produced by CHO cells or yeast or plant expression. The recombinant human hyaluronidase obtained by these production methods can meet the requirements for safety and activity, and besides, the LMW-HA fragment injections produced by these production methods have been validated by clinical practices in human, and have shown effective therapeutic effects without allergy and side effect.

Finally, it shall be explained that the above are only the optimal embodiments of the invention and are not used for limiting the invention. Although the invention is explained in details in reference to the previous embodiments, the technicians of this field can amend the technical schemes recorded in the previous embodiments or perform equivalent substitution for part of the technical features. Any amendment, equivalent substitution, improvement, etc. within the energy and principles of the invention shall be within the protective scope of the invention.

What is claimed is:

1. A method for treating pain or pruritus using a low-molecular weight hyaluronic acid (LMW-HAI) drug injection, the method comprising: preparing the LMW-HA drug injection and administering the LMW-HA drug injection to treat the pain or the pruritus, wherein the LMW-HA drug infection comprises underivatized LMW-HA fragments with a molecular weight distribution consisting of 10-60 KD, further wherein the LMW-HA fragments are obtained by a process comprising:
   a) directly digesting a high-molecular-weight hyaluronic acid (HMW-HA) raw material having a molecular weight distribution of 800-1,200 KD using a recombinant hyaluronidase PH20;
   b) performing a first thermal treatment at 84-95° C. for inactivation of the recombinant human hyaluronidase PH20, bacteria and viruses; and either
   c-i) performing a second thermal treatment at less than 105° C.; or
   c-ii) not performing a second thermal treatment.

2. The method of claim 1, wherein the LMW-HA drug injection comprises inactivated hyaluronidase PH20 fragments.

* * * * *